(12) United States Patent
Higgins et al.

(10) Patent No.: US 7,655,431 B2
(45) Date of Patent: Feb. 2, 2010

(54) COMPOSITIONS AND METHODS BASED UPON THE KINASE HASPIN

(75) Inventors: Jonathan Higgins, West Roxbury, MA (US); Jun Dai, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 11/792,258

(22) PCT Filed: Dec. 5, 2005

(86) PCT No.: PCT/US2005/043790

§ 371 (c)(1),
(2), (4) Date: Dec. 6, 2007

(87) PCT Pub. No.: WO2006/062855

PCT Pub. Date: Jun. 15, 2006

(65) Prior Publication Data

US 2008/0096222 A1    Apr. 24, 2008

Related U.S. Application Data

(60) Provisional application No. 60/634,259, filed on Dec. 9, 2004.

(51) Int. Cl.
*C12Q 1/48* (2006.01)
*C12N 9/12* (2006.01)
(52) U.S. Cl. .................................. 435/15; 435/194
(58) Field of Classification Search ................ None
See application file for complete search history.

(56) References Cited

FOREIGN PATENT DOCUMENTS

| WO | WO0218418 | * | 3/2002 |
| WO | WO03070894 | * | 8/2003 |

OTHER PUBLICATIONS

Tanaka et al, Identification and characterization of a haploid germ cell-specific nuclear protein kinase (Haspin) in spermatid nuclei and its effects on somatic cells. J Biol Chem. Jun. 11, 1999;274(24):17049-57.*
Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Benyunes et al, Characterization of an oligopeptide chemoattractant receptor on human blood monocytes using a new radioligand. Blood. Mar. 1984;63(3):588-92.*
International Search Report for PCT/US05/43790 filed Dec. 5, 2005.
Written Opinion of the International Searching Authority for PCT/US05/43790 filed Dec. 5, 2005.
Adams, et al., "Essential Roles of *Drosophila* Inner Centromere Protein (INCENP) and Aurora B in Histone H3 Phosphorylation, Metaphase Chromosome Alignment, Kinetochore Disjunction, and Chromosome Segregation," *J. Cell Bio*. 153:865-880 (May 2001).
Andrews, et al., "Mitotic Mechanisms: The Auroras Come Into View," Curr. Opin. Cell Bio. 15:672-683 (2003).
Carmena, et al., "The Cellular Geography of Aurora Kinases," *Nat. Rev. Mol. Cell. Bio*. 4:842-854 (Nov. 2003).
Clayton, et al., "MAP Kinase-Mediated Phosphoacetylation of Histone H3 and Inducible Gene Regulation," *FEBS Lett*. 546:51-58 (2003).
Crosio, et al., "Mitotic Phosphorylation of Histone H3: Spatio-Temporal Regulation by Mammalian Aurora Kinases," *Mol. Cell. Bio*. 22:874-885 (Feb. 2002).
Desouza, et al., "Mitotic Histone H3 Phosphorylation by the NIMA Kinase in *Aspergillus nidulans*," *Cell* 102:293-302 (Aug. 2000).
Ditchfield, et al., "Aurora B Couples Chromosome Alignment with Anaphase by Targeting BubR1, Mad2, and Cenp-E to Kinetochores," *J. Cell. Bio*. 161:267-280 (Apr. 2003).
Giet, et al., "*Drosophila* Aurora B Kinase is Required for Histone H3 Phosphorylation and Condensin Recruitment During Chromosome Condensation and to Organize the Central Spindle During Cytokinesis," J. Cell Biol. 152:669-682 (Feb. 2001).
Goto, et al., "Identification of a Novel Phosphorylation Site on Histone H3 Coupled with Mitotic Chromosome Condensation," *J. Biol. Chem*. 274:25543-25549 (Sep. 1999).
Goto, et al., "Aurora-B Phosphorylates Histone H3 at Serine28 with Regard to the Mitotic Chromosome Condensation," *Genes Cells* 7:11-17 (2002).
Hauf, et al., "The Small Molecule Hesperadin Reveals a Role for Aurora B in Correcting Kinetochore-Microtubule Attachment and in Maintaining the Spindle Assembly Checkpoint," *J. Cell Biol*. 161:281-294 (Apr. 2003).
Hendzel, et al., "Mitosis-Specific Phosphorylation of Histone H3 Initiates Primarily Within Pericentromeric Heterochromatin During G2 and Spreads in an Ordered Fashion Coincident with Mitotic Chromosome Condensation," *Chromosoma* 106:348-360 (1997).
Higgins, et al., "Structure, Function and Evolution of Haspin and Haspim-Related Proteins, a Distinctive Group of Eukaryotic Protein Kinases," *Cell. Mol. Life Sci*. 60:446-462 (2003).
Higgins, et al., "The Haspin Gene: Location in an Intron of the Integrin αE Gene, Associated Transcription of an Integrin αE-Derived RNA and Expression in Diploid as well as Haploid Cells," *Gene* 267:55-69 (2001).
Higgins, et al., "Haspin-Like Proteins: A New Family of Evolutionary Conserved Putative Eukaryotic Protein Kinases," *Prot. Sci*. 10:1677-1684 (2001).
Hsu, et al., "Mitotic Phosphorylation of Histone H3 is Governed by Ipl1/aurora Kinase and Glc7/PP1 Phosphatase in Budding Yeast and Nematodes," *Cell* 102:279-291 (Aug. 2000).

(Continued)

*Primary Examiner*—Sheridan Swope
(74) *Attorney, Agent, or Firm*—Law Office of Michael A. Sanzo, LLC

(57) ABSTRACT

The present invention is directed to methods for increasing or decreasing the phosphorylation of histone H3 using factors that alter the activity of the kinase haspin. The invention includes assays for identifying inhibitors, peptides that can serve as inhibitors or in the generation of antibodies that specifically recognize phosphorylated histone, polynucleotides encoding peptides, procedures for increasing intracellular haspin levels, and methods for assaying haspin activity in a biological sample to determine whether abnormalities in cell division may be due to the overexpression or underexpression of haspin.

10 Claims, 3 Drawing Sheets

OTHER PUBLICATIONS

Jenuwein, et al., "Translating the Histone Code," *Science* 293:1074-1080 (Aug. 2001).

Nigg, et al., "Mitotic Kinases as Regulators of Cell Division and its Checkpoints," *Nat. Rev. Mol. Cell Biol.* 2:21-32 (Jan. 2001).

Peterson, et al., "The *S. pombe* Aurora-Related Kinase Ark1 Associates with Mitotic Structures in a Stage Dependent Manner and is Required for Chromosome Segregation," *J. Cell Sci.* 114:4371-4384 (2001).

Polioudaki, et al., "Mitotic Phosphorylation of Histone H3 at Threonine 3," *FEBS Lett.* 560:39-44 (2004).

Preuss, et al., "Novel Mitosis-Specific Phosphorylation of Histone H3 at Thr11 Mediated by D1k/Z1P Kinase," *Nucleic Acids Res.* 31:878-885 (2003).

Prigent, et al., "Phosphorylation of Serine 10 in Histone H3, What for?" *J. Cell Sci.* 116:3677-3685 (2003).

Shannon, et al., "Chromosome Dynamics: New Light on Aurora B Kinase Function," *Curr. Biol.* 12:R458-R460 (Jul. 2002).

Shoemaker, et al., "H3-Specific Nucleohistone Kinase of Bovine Thymus Chromatin," *J. Biol. Chem.* 255:11048-11055 (1980).

Tanaka, et al., "Identification and Characterization of a Haploid Germ Cell-Specific Nuclear Protein Kinase (Haspin) in Spermatid Nuclei and Its Effects on Somatic Cells," *J. Biol. Chem.* 274:17049-17057 (Jun. 1999).

Tanaka, et al., "Isolation and Characterization of cDNA Clones Specifically Expressed in Testicular Germ Cells," *FEBS Lett.* 355:4-10 (1994).

Turner, et al., "Cellular Memory and the Histone Code," *Cell* 111:285-291 (Nov. 1, 2002).

Van Hosser, et al., "Histone H3 Phosphorylation is Required for the Initiation, but not Maintenance of Mammalian Chromosome Condensation," *J. Cell Sci.* 111:3497-3506 (1998).

Wei, et al., "Phosphorylation of Histone H3 is Required for Proper Chromosome Condensation and Segregation," *Cell* 97:99-109 (Apr. 1999).

Yoshimura, et al., "Nested Genomic Structure of Haploid Germ Cell Specific *haspin* Gene," *Gene* 267:49-54 (2001).

Zeitlin, et al., "CENP-A is Phosphorylated by Aurora B Kinase and Plays an Unexpected Role in Completion of Cytokinesis," *J. Cell Biol.* 155:1147-1157 (Dec. 2001).

Supplementary European Search Report for EP 05 85 2875, Jun. 2, 2008.

\* cited by examiner

```
MAASLPGPGS RLFRTYGAAD GRRQRRPGRE AAQWFPPQDR RRFFNSSGSS DASIGDPSQS
DDPDDPDDPD FPGSPVRRRR RCPGGRVPKD RPSLTVTPKR WKLRARPSLT VTPRRLGLRA
RPPQKCSTPC GPLRLPPFPS RDSGRLSPDL SVCGQPRDGD ELGISASLFS SLASPCPGSP
TPRDSVISIG TSACLVAASA VPSDLHLPEV SLDRASLPCS QEEATGGAKD TRMVHQTRAS
LRSVLFGLMN SGTPEDSEFR ADGKNMRESC CKRKLVVGNG PEGPGLSSTG KRRATGQDSC
QERGLQEAVR REHQEASVPK GRIVPRGTDR LERTRSSRKS KHQEATETSL LHSHRFKKGQ
KLGKDSFPTQ DLTPLQNACF WTKTRASFSF HKKKIVTDVS EVCSIYTTAT SLSGSLLSEC
SNRPVMNRTS GAPSSWHSSS MYLLSPLNTL SISNKKASDA EKVYGECSQK GPVPFSHCLP
TEKLQRCEKI GEGVFGEVFQ TIADHTPVAI KIIAIEGPDL VNGSHQKTFE EILPEIIISK
ELSLLSGEVC NRTEGFIGLN SVHCVQGSYP PLLLKAWDHY NSTKGSANDR PDFFKDDQLF
IVLEFEFGGI DLEQMRTKLS SLATAKSILH QLTASLAVAE ASLRFEHRDL HWGNVLLKKT
SLKKLHYTLN GKSSTIPSCG LQVSIIDYTL SRLERDGIVV FCDVSMDEDL FTGDGDYQFD
IYRLMKKENN NRWGEYHPYS NVLWLHYLTD KMLKQMTFKT KCNTPAMKQI KRKIQEFHRT
MLNFSSATDL LCQHSLFK
```

Figure 1

```
gcgtttgaac ctcttggcgg gtgccggcca tggcggcttc gctcccggga cctgggagcc
ggcttttccg cacatatggg gctgcggacg gcaggagaca gcggcggccg ggccgggaag
ccgcgcagtg gttcccgccg caggaccgga ggcgtttctt caacagcagc ggcagcagcg
acgccagcat cggcgacccc tcgcagtccg acgatcctga cgatcccgac gaccccgact
tccccggcag cccggtgagg cggcggcgga ggtgtccgg cggccgagtg cccaaggacc
ggcccagcct gaccgtgacc ccaaagcgct ggaagctgcg agctcgccca agcctaaccg
tgacccaag acgcctgggg ctgcgagctc ggcccccgca gaagtgcagc acccctgcg
gcccgctccg acttccgccc ttccccagcc gcgactccgg ccgcctcagc ccggacctca
gcgtgtgcgg ccagcccagg gacggcgacg agctgggcat cagtgcctcc ctgttcagct
ctctggcctc gccctgcccc gggtcccaa cgccaaggga cagtgtcatc tcgatcggca
cctccgcctg tctggttgca gcctcagccg tcccgagcga cctccacctc cagaagtct
ccctggaccg agcatctctc ccctgctccc aggaggaagc gacaggagga gccaaggaca
ccaggatggt ccaccaaacc cgcgccagcc tcaggtcagt tctctttggc cttatgaact
caggaacccc tgaggattct gagtttcggg cagatgggaa gaatatgaga gagtcctgct
gtaaaaggaa actggtggtg ggaaatggac cagagggtcc aggtctgtca agcacaggca
agaggagggc cacaggccag gactcttgtc aagagagagg gcttcaagag gccgtccgga
gagagcatca ggaggccagt gttcccaagg gccgcattgt gccaagggga acagacaggc
tggagagaac tagatcaagc cggaagagca aacatcagga ggcaacggaa acctctctcc
tccattccca ccgctttaaa aagggccaaa agctgggaaa agattcgttc cccacccagg
acctgactcc tttacagaat gcctgctttt ggaccaaaac cagggcttcc ttcagtttcc
acaagaagaa aattgtgact gatgtgtcag aggtctgcag catctatacc actgccactt
ctctctctgg atccctccta tcagaatgtt caaaccggcc tgtcatgaac agaacaagtg
gtgctccgtc ctcttggcac tcctcctcta tgtatttgct aagccccta aacactctaa
gtatttcaaa caaaaaggca tctgatgctg aaaaggttta tggggaatgc agtcagaagg
gtcctgtccc ctttagccat tgccttccca cagaaaaact gcaacgctgt gagaagattg
gggaaggggt gtttggcgaa gtgtttcaaa caattgctga tcacacaccc gtagccataa
aaatcattgc tattgaagga ccagatttag tcaatggatc ccatcagaaa acctttgagg
aaatcctgcc agagatcatc atctccaaag agttgagcct cttatccggt gaagtgtgca
accgcacaga aggctttatc gggctgaact cagtgcactg tgtccaggga tcttaccctc
ccttgctcct caaagcctgg gatcactata attcaaccaa aggctctgca aatgaccggc
ctgatttttt taaagacgac cagctcttca ttgtgctgga atttgagttt ggagggattg
acttagagca aatgcgaacc aagttgtctt ccttggctac tgcaaagagc attctacacc
agctcacagc ctcctcgca gtggcagagg catcactgcg cttgagcac cgagacttac
actggggaa cgtgctctta aagaaaacca gcctcaaaaa actccactac accctcaatg
ggaagagcag cactatcccc agctgtgggt tgcaagtgag catcattgac tacaccctgt
cgcgcttgga acgggatggg attgtggttt tctgtgacgt ttccatggat gaggacctgt
ttaccggtga cggtgactac cagtttgaca tctacaggct catgaagaag gagaataaca
accgctgggg tgaatatcac ccttatagta atgtgctctg gttacattac ctgacagaca
agatgctgaa acaaatgacc ttcaagacta aatgtaacac tcctgccatg aagcaaatta
agagaaaaat ccaggagttc cacaggacaa tgctgaactt cagctctgcc actgacttgc
tctgccagca cagtctgttt aagtaagcta aatgtatctt actgcccga aatgagagga
gactggtctt gaagcctctg gtgctgtttc aacctccgtc cccacaggag ggtggaactc
ccattctcac aggtttccag tcagcttttc aaacaagaat tttgtttcca aatggaaact
gaaatatttg ttgaaatgtt taaatttgct gataacaaat gttctgaaag aagtaaacta
gccgggcgca gtggcgtgcg cctgtagtcc cagctactcg ggaggctgag gcaggaggat
cgcttgagcc caagagttca tatctagcct ggtcaacata gcaagacccc tgtctctatt
tttttaaata aataaactac atgtgaaaac aaaaaaaaaa aaaaaaaaaa aaaaaaaaa
```

Figure 2 martkqtark stggkaprkq latkaarksa patggvkkph ryrpgtvalr eirryqkste
llirklpfqr lvreiaqdfk tdlrfqssav malqeaceay lvglfedtnl caihakrvti
mpkdiqlarr irgera

Figure 3 atggctcgta ctaaacagac agctcggaaa tccaccggcg gtaaagcgcc acgcaagcag
ctggctacca aggctgctcg caagagcgcg ccggctaccg gcggcgtgaa aaagcctcac
cgttaccgcc cgggcactgt ggctctgcgc gagatccgcc gctaccaaaa gtcgaccgag
ttgctgattc ggaagctgcc gttccagcgc ctggtgcgag aaatcgccca agacttcaag
accgatcttc gcttccagag ctctgcggtg atggcgctgc aggaggcttg tgaggcctac
ttggtagggc tctttgagga cacaaaacctt tgcgccatcc atgctaagcg agtgactatt
atgcccaaag acatccagct cgctcgccgc attcgcggag aaagagcgta aatgtaaagt
cacttttttca tcagtcttaa aacccaaagg ctctttttcag agccacccac tt

Figure 4

COMPOSITIONS AND METHODS BASED UPON THE KINASE HASPIN

CROSS REFERENCE TO RELATED APPLICATIONS

The present application represents U.S. national stage of international application PCT/US2005/043790, which had an international filing date of Dec. 5, 2005, and which was published in English under PCT Article 21(2) on Jun. 15, 2006. The international application claims priority to U.S. provisional application 60/634,259, filed on Dec. 9, 2004. These prior applications are hereby incorporated by reference in their entirety.

FIELD OF THE INVENTION

The present invention is directed to assays for identifying factors that inhibit the phosphorylation of histone H3 by haspin. It includes peptides that act as inhibitors of haspin and polynucleotides that encode these peptides. Phosphorylated forms of the peptides may be used to generate antibodies that specifically recognize histone H3 after it has undergone phosphorylation and these antibodies may be used in assays that measure haspin activity. In addition, the invention includes methods for inhibiting haspin activity based upon the use of small interfering RNAs.

BACKGROUND OF THE INVENTION

Errors during cell division can lead to genomic instability and aneuploidy, contributing to the generation of cancer and birth defects. A select group of kinases has been found to orchestrate mitosis. In particular, members of the cyclin-dependent kinase, Aurora, Polo, and NIMA/Nek families phosphorylate substrates in chromatin and at the spindle apparatus to regulate events during cell division (Nigg, *Nat. Rev. Mol. Cell. Biol.* 2: 21-32 (2001)).

Not surprisingly, histones are major targets of mitotic kinases. For example, histone H3 is extensively phosphorylated at serine-10 during mitosis and meiosis (Hendzel, et al., *Chromosoma* 106:348-360 (1997); Prigent, et al., *J. Cell Sci.* 116:3677-3685 (2003)). The function of this modification is debated, but it may facilitate chromatin condensation or the release of cohesin and ISWI chromatin-remodeling ATPases (Van Hooser, et al., *J. Cell Sci.* 111:3497-506 (1998); Andrews, et al., *Curr. Opin. Cell Biol.* 15:672-683 (2003); Prigent, et al., *J. Cell Sci.* 116:3677-3685 (2003); Swedlow, et al., *Mol. Cell.* 11:557-569 (2003)). A *Tetrahymena* strain with histone H3 mutated at serine-10 showed perturbed chromatin condensation and abnormal chromosome segregation during meiosis and mitosis (Wei, et al., *Cell* 97:99-109 (1999)), while a similar mutation in *S. cerevisiae* had no such effect (Hsu, et al., *Cell* 102:279-291 (2000)). Therefore, histone phosphorylation at serine-10 has an important role in mitosis but the extent to which it is required appears species-dependent, perhaps because of redundancy provided by other mitotic histone modifications ((Hsu, et al., *Cell* 102:279-291 (2000)). In fact, a number of highly conserved serine and threonine residues that might be phosphorylated are found in the core histones of all eukaryotes. Mitotic phosphorylation of threonine-11 (Preuss, et al., *Nucleic Acids Res.* 31:878-885 (2003)) and serine-28 (Goto, et al., *J. Biol. Chem.* 274:25543-25549 (1999)) of H3 has been reported.

The identities of protein kinases that phosphorylate the histones during mitosis in vivo remain somewhat uncertain. The best studied is aurora B, a "chromosome passenger protein" that is located on the chromosomes during prophase and becomes concentrated at inner centromeres by metaphase before relocalizing to the spindle midzone at anaphase (Carmena, et al., *Nat. Rev. Mol. Cell. Biol.* 4:842-854 (2003)). Consistent with this, aurora B has both chromatin and spindle-associated substrates and influences mitosis at a number of steps. Aurora B homologues play an important role in ensuring chromosome bi-orientation at metaphase by correcting mono-orientated attachments to the spindle, and are involved in normal chromatid separation and cytokinesis (Shannon, et al., *Curr. Biol.* 12:R458-460 (2002); Andrews, et al., *Curr. Opin. Cell. Biol.* 15:672-683 (2003)). They are also required for phosphorylation of the centromeric histone variant CENP-A at serine-7 and of histone H3 at serine-10 in many organisms (Hsu, et al., *Cell* 102:279-291 (2000); Adams, et al., *J Cell Bio.* 153:865-880 (2001); Giet, et al., *J. Cell Biol.* 152:669-682 (2001); Petersen, et al., *J. Cell Sci.* 114:4371-4384 (2001); Zeitlin, et al., *J. Cell Biol.* 155:1147-1157 (2001); Crosio, et al., *Mol. Cell. Biol.* 22:874-875 (2002); Ditchfield, et al., *J. Cell Biol.* 161:267-280 (2003); Hauf, et al., *J. Cell Biol.* 161:281-294 (2003)).

It has not been possible, however, to unambiguously assign the role of mitotic histone H3 serine-10 phosphorylation solely to aurora B (Nigg 2001; Prigent and Dimitrov 2003). Indeed, in *Aspergillus*, mitotic histone H3 serine-10 phosphorylation is dependent on the kinase NIMA (De Souza, et al., *Cell* 102:293-302 (2000)). In addition, kinases that bring about the phosphorylation of other histone residues during mitosis must exist. The nature of these key enzymes remains unclear, although there is some evidence that aurora B and the Dlk/ZIP kinase are responsible for mitotic phosphorylation of H3 serine-28 and threonine-11 respectively (Goto, et al., *Genes Cells* 7:11-17 (2002); Preuss, et al., *Nucleic Acids Res.* 31:878-885 (2003)).

Haspin/Gsg2 (Haploid Germ Cell-Specific Nuclear Protein Kinase/Germ Cell Specific Gene-2) was first identified as a testis-specific gene in mice (Tanaka, et al., *FEBS Letts.* 355:4-10 (1994); Tanaka, et al., *J. Biol. Chem.* 274:17049-17057 (1999)). More recent work has suggested that lower levels of haspin mRNA are also present in other organs and in all proliferating cell lines tested, suggesting that expression of haspin is not truly haploid germ cell-specific (Higgins, *Gene* 267:55-69 (2001). Genes encoding haspin homologs are present in all major eukaryotic phyla, including yeasts, microsporidia, plants, nematodes, flies, fish, amphibians and mammals (Higgins, *Cell Mol. Life. Sci.* 60:446-462 (2003)). These haspin genes encode proteins that contain a distinctive C-terminal putative kinase domain and together constitute a novel eukaryotic protein kinase family (Higgins, *Prot. Sci.* 10:1677-1684 (2001). The N-terminal portion of the haspin proteins is less conserved between species and has no clear homology to known domains (Tanaka, et al., *J. Biol. Chem.* 274:17049-17057 (1999); Yoshimura, et al., *Gene* 267:49-54 (2001); Higgins, *Cell Mol. Life. Sci.* 60:446-462 (2003)).

SUMMARY OF THE INVENTION

The present invention is based upon the discovery that the protein kinase responsible for phosphorylating histone H3 at threonine-3 is haspin. When levels of haspin are abnormally low, chromosomal alignment does not occur at metaphase. If haspin levels are abnormally high, there is a delay in the cell cycle during mitosis prior to the time that cells enter metaphase. Thus, either too much or too little haspin can lead to serious defects in cell division. The full length sequences for human histone H3 and for human haspin have been previously reported.

In its first aspect, the invention is directed to an assay for determining if a test compound inhibits the phosphorylation of human histone H3 by haspin. This is accomplished by incubating a solution containing haspin and a polypeptide that serves as a substrate for haspin phosphorylation. The haspin is preferably human and may be purified from natural sources, recombinantly produced or chemically synthesized. The polypeptide used in assays should be 5-135 (and preferably 8-135) amino acids in length and have the N-terminal sequence ARTKQ (SEQ ID NO:4). This N-terminal sequence may be extended at its C terminal end by between 1 and 130 amino acids which are sequentially added according to the H3-derived sequence:

(SEQ D NO:21)
TARKSTGGKAPRKQLATKAARKSAPATGGVKKPHRYRPGTVALREIRRYQ

KSTELLIRKLPFQRLVREIAQDFKTDLRFQSSAVMALQEACEAYLVGLFE

DTNLCAIHAKRVTIMPKDIQLARRIRGERA.

In addition a single methionine may optionally be added to SEQ ID N:4 as the N-terminal amino acid and may also be included in any of the extended peptides. The final length of polypeptides is preferably 8-45 amino acids. Thus, preferred peptides would include those 8, 21 and 45 residues long. If desired, threonines and serines, other than thr-3 may be replaced with an amino acid that cannot undergo phosphorylation, e.g., alanine. This will ensure that only phosphorylation at position 3 is measured in assays.

The incubations performed in the haspin assays should be carried out under conditions suitable for phosphorylation and in the presence of test compound, ideally at several different concentrations. At the end of the incubation, the amount of phosphorylation of H3 that has occurred is determined. This can be accomplished using assays that are well known in the art and which are described herein in the Examples section. In general, such assays involve performing incubations using $^{32}$P-labeled ATP. The radioactive phosphorous is transferred to the polypeptide containing the H3 phosphorylation site and, at the end of the incubation, the polypeptide is isolated and the amount of radioactivity present is determined. The polypeptides that can be used include histone H3 itself, peptides representing the amino terminus of H3 as described above, and larger polypeptides which include these peptides, e.g. H3-glutathione-S-transferase ("H3-GST"). In determining whether a test compound inhibits the enzymatic activity of haspin, "control" incubations should also be performed which are similar to those described above, but which are carried out in the absence of the test compound. By comparing the amount of phosphorylation that occurs both in the presence and the absence of the test compound, a conclusion can be reached as to whether inhibition has occurred.

Many variations of the assay described above will be apparent to those of skill in the art. For example, the phosphorylation region of H3 histone, i.e., the N-terminal 8, 21 or 45 amino acids, can be joined either directly or indirectly to a component such as biotin that aids in separation at the conclusion of incubations, or to a carrier protein other than GST. Quantitative analysis of the amount of radioactivity associated with polypeptides can be determined using a radioactivity counter or by autoradiography after electrophoresis.

In another aspect, the invention is directed to substantially pure peptides with sequences corresponding to those described above in connection with assays of haspin activity. Each peptide should include the H3N-terminal sequence ARTKQ (SEQ ID NO:4), be between 5 and 135 residues in length, inhibit the phosphorylation of human histone H3 by haspin, and not be histone H3 itself. The ARTKQ sequence may be extended from 1 to 130 amino acids in the C-terminal direction with amino acids being added sequentially according to SEQ ID NO:21. Polypeptides made in this manner will have, for example, lengths of 8-134 amino acids, 8-45 amino acids, and 8-20 amino acids. The threonine that appears in SEQ ID NO:4 between arginine and lysine is the site of phosphorylation and the three residues RTK should generally be present (although it may be possible to introduce some modifications, such as methylation or perhaps to make a conservative substitution and still maintain activity). Peptides that are included in the invention include ARTKQTAR (SEQ ID NO:1); ARTKQTA (SEQ ID NO:2); ARTKQT (SEQ ID NO:3); ARTKQ (SEQ ID NO:4); RTKQTAR (SEQ ID NO:5); RTKQTA (SEQ ID NO:6); and RTKQT (SEQ ID NO:7). Any of the peptides may also include an additional methionine as the N-terminal residue. For recombinant forms such as H3-GST, a methionine is necessary as a start codon. This may or may not be removed in the expression system. Thus when peptides are recombinantly made in an expression system and then isolated the N-terminal methionine derived from the start codon may be present.

The peptides will compete with H3 histone for haspin and can therefore be used as inhibitors of haspin kinase activity. Thus, they may serve as positive controls in the assays for identifying new inhibitors of phosphorylation. The peptides will also be useful in the development of antibodies that bind with specificity to phosphorylated forms of H3 as described in greater detail below.

In order to block haspin kinase activity within cells, polynucleotides encoding the peptides described above can be made and incorporated into a vector in which they are operably linked to a promoter, i.e., they may be incorporated into an "expression vector." The term "operably linked" means that the coding sequence is under the control of the promoter and joined in such a manner that transcription produces a product that is correctly translated into the encoded peptide. The vector may be used to transfect a host cell where the effect of inhibiting histone phosphorylation will be examined. As an alternative, cells may be transfected with either small interfering RNAs (SiRNAs) that reduce haspin levels or with polynucleotides encoding these SiRNAs. Methods for designing effective SiRNAs are well known in the art (Gong et al., *Trends Biotechnology*. 22(9):451-4 (2004); Reynolds, et al., *Nat. Biotechnol*. 22(3):326-30 (2004); Bertrand, et al., *Methods Mol. Biol*. 288:411-30; Gilmore, et al., *J. Drug Target*. 12(6):315-40 (2004)) and may be based upon the previously reported human haspin sequence (see FIG. 2).

In another aspect, the invention includes a substantially pure peptide or protein comprising any of the amino acid sequences described above but in which thr-3 is phosphorylated. For example, the invention includes the peptide AR(pT)KQTAR (SEQ ID NO:8), wherein pT designates phosphorylated threonine. The peptide or protein should not be phosphorylated histone H3 itself but should be capable of inducing the generation of antibodies that bind to phosphorylated H3 when administered to an appropriate animal, e.g., a mouse, rabbit, goat, etc. The AR(pT)KQTAR sequence may be incorporated into a longer sequence, i.e., 8-20 amino acids in length. In addition, peptides for the generation of antibodies may be selected from the group consisting of: AR(pT)KQTA (SEQ ID NO:9); AR(pT)KQT (SEQ ID NO:10); AR(pT)KQ (SEQ ID NO:11); R(pT)KQTAR (SEQ ID NO:12); R(pT)KQTA SEQ ID NO: 13); and R(pT)KQT (SEQ ID NO:14). As discussed previously, methionine may also be present as the N-terminal amino acid.

The invention includes methods of making an antibody that specifically recognizes phosphorylated human histone H3 by administering one of the phosphorylated peptides to an animal at a dosage and for a duration effective to induce antibody production. The term "specifically recognizes" indicates an antibody that binds with at least 100 fold greater affinity to the phosphorylated form of the histone as compared to the non-phosphorylated form. Protocols for different animals used in antibody production are well known in the art and can be used in conjunction with the present invention. The method also includes a step in which antibody that binds to the phosphorylated form of histone but not to the non-phosphorylated form is selected. The selection process may involve depleting a population of polyclonal antibodies using immobilized non-phosphorylated peptides. Screening procedures in which comparisons are made between the binding of antibody to phosphorylated and non-phosphorylated proteins and peptides and to proteins and peptides carrying modifications of surrounding residues (for example, methylation and/or acetylation of Arg-2, Lys-4) may also be performed regardless of whether polyclonal or monoclonal antibodies are produced.

The inhibitors of histone phosphorylation described above will be useful to scientists and clinicians studying cell division and particularly in experiments designed to examine the causes of abnormal mitosis and ways to correct the abnormalities. However, methods for increasing the phosphorylation of histone H3 will also be useful. Thus, the invention also includes methods in which cells are transfected with an expression vector comprising nucleotides encoding human haspin operably linked to a promoter, preferably an inducible promoter.

Assays of haspin activity may be used to determine whether a biological sample contains cells undergoing abnormal division or in assessing a sample of abnormal cells to determine the cause of the abnormality, i.e., whether it can be attributed, in part, to too much, or too little, haspin activity. The method involves obtaining a biological sample and determining the amount of haspin activity present using methods that are well known in the art (see Examples section). The antibodies described above which distinguish between phosphorylated and non-phosphorylated histone H3 may be used in evaluating haspin activity. The results obtained from the biological sample should be compared with results from control samples known to be free of abnormal cells, with results obtained from the general population or from some other control group selected using standard methods. If this comparison reveals an excessively high or low level of haspin activity, then it may be concluded that the biological sample contains cells that are subject to abnormal mitosis or that abnormalities in cell division may be attributed, at least in part, to defects associated with haspin.

The compositions and methods described above will be useful not only as tools for scientists studying cell division, but also in the development of new drugs and procedures for the treatment or prevention of diseases associated with abnormal cell division. Thus, modulators of haspin have potential use as agents for the prevention or treatment of diseases such as cancer. Assays may be coupled with treatments to select patients most likely to respond. For example, cells undergoing abnormal mitosis that are found to have excessively high haspin levels would generally be considered more likely to respond to a haspin inhibitor than cells in which the activity is not elevated.

BRIEF DESCRIPTION OF THE DRAWINGS

FIG. 1 shows the amino acid sequence of human haspin (SEQ ID NO:17, Higgins, *Gene* 267:55-69 (2001)). Here and throughout this document peptide sequences begin with the N-terminus on the left side and extend toward the C-terminus.

FIG. 2 shows the nucleotide sequence of the human haspin gene (SEQ ID NO:18, Higgins, *Gene* 267:55-69 (2001)).

FIG. 3 shows the amino acid sequence of human histone H3 (SEQ ID NO:19, Lusic, et al., *EMBO J.* 22:6550-6561 (2003)). The N-terminal methionine should usually be removed during protein processing and numbering of the protein therefore begins with the alanine residue. The site of phosphorylation by haspin is at the threonine in the third position, i.e. "threonine-3" or "thr-3." The arginine (R) and lysine (K) residues immediately adjacent to thr-3 are also necessary for phosphorylation. Threonine and serine residues other than thr-3 may be replaced with an amino acid incapable of undergoing phosphorylation, e.g., alanine without affecting haspin activity.

FIG. 4 shows the gene sequence for human histone H3 (SEQ ID NO:20, Lusic, et al., *EMBO J.* 22:6550-6561 (2003)).

DETAILED DESCRIPTION OF THE INVENTION

During the last several years, it has become apparent that protein kinases phosphorylating specific sites on histones play an important role in regulating mitosis. Errors resulting in the misalignment of chromosomes and other abnormalities may contribute to the generation of cancer and birth defects.

The present invention is based upon the identification of the protein haspin as the kinase responsible for phosphorylating a specific threonine residue on histone H3. Defects in this phosphorylation are associated with abnormalities in mitosis. Thus, significant changes in cell division become apparent when haspin levels are either abnormally high or abnormally low. Methods and compositions for studying this process will help scientists understand how cell division is regulated and may lead to the development of new therapeutic and diagnostic approaches of clinical importance.

I. Inhibitors of Haspin Kinase Activity

Peptides for inhibiting the activity of haspin have been designed based upon the specific site at which this enzyme interacts with histone H3. The most preferred peptide sequence for use as an inhibitor is: ARTKQTAR (SEQ ID NO:1). However, the sequence may be incorporated into larger polypeptides or compounds or it may be shortened somewhat, provided that the final sequence is at least five residues in length and that, in general, the RTK core sequence is maintained. However, it may be possible to introduce minor variations in this core or to add non-peptidic elements. It is recognized in the art that changes can be made to peptide sequences to introduce conformational constraints, increase inhibitory potency, alter solubility, stability, pharmacokinetics etc. In addition, sequences shorter than 8 or even 5 amino acids may still be useful as components of a larger compound.

The peptides can be made by solid-phase peptide synthesis using standard N-tert-butyoxycarbonyl (tBoc) chemistry. Altered amino acids or non-amino acid agents to increase inhibitory potency, selectivity, pharmacokinetics, or to aid in the purification of peptides (e.g., biotin) may also be included using standard methods. Peptide sequences may be attached by a linker to an ATP analog (so-called "bisubstrate inhibitors") and have much higher potency. Once inhibitors have been synthesized, they can be purified using procedures such as high pressure liquid chromatography on reverse-phase columns or by other procedures well known in the art. Purity may be assessed by HPLC and the presence of the correct composition be confirmed by mass spectrometry. Inhibitory peptides may be used in in vitro assays such as those described herein in the Examples section, serve as positive controls in assays for identifying new inhibitors and have potential value as therapeutic agents.

In order to study the intracellular effect of inhibitors, a DNA sequence encoding an inhibitory peptide may be placed in a vector containing transcriptional and translational signals recognized by the host. Appropriate vectors and techniques for cloning and expressing proteins and peptides are well known in the art of molecular biology. The vectors may be introduced into host cells, preferably mammalian host cells, by methods such as calcium phosphate precipitation, microinjection, electroporation or viral transfer. Cells expressing the peptides can be selected using standard, well established methods. One method for confirming the presence of the peptide-encoding nucleic acid in cells is to perform polymerase chain reaction (PCR) amplification using appropriately selected primers. Incorporation of phosphate into histone H3 can be determined by Western blotting of cell lysates using antibodies specific for the phosphorylated protein and quantification by enhanced chemiluminescence, or by precipitating histone H3 from lysates of cells grown in the presence of $^{32}P$ using antibodies specific for the phosphorylated protein and then counting radioactivity in the precipitate.

Inhibition of histone H3 can also be studied using small interfering RNAs which are designed to inhibit the expression of haspin. Standard methods for designing inhibitory RNAs have been described in the art and may be based upon the known haspin sequence. Methods that can be employed for studying the effect of the SiRNAs are described in the Examples section.

II. Antibodies

A preferred method for producing antibodies that bind to phosphorylated histone H3 but not to its non-phosphorylated counterpart is described in the Examples section. One method involves injecting animals with phosphorylated peptides derived from the site at which haspin interacts with histone. After isolating the antibodies, those that bind to the non-phosphorylated form of H3 may be removed using either the histone itself or a phosphorylation site peptide that has been immobilized on a solid support. Screening assays may be performed in which the binding of antibody to phosphorylated peptide is compared to non-phosphorylated.

Methods for making and detecting antibodies are well known to those of skill in the art as evidenced by standard reference works such as: Harlow, et al., *Antibodies, A Laboratory Manual*, Cold Spring Harbor Laboratory, NY (1988); and Campbell, "Monoclonal Antibody Technology" in *Laboratory Techniques in Biochemistry and Molecular Biology* (1984).

The term "antibody," as used herein, is meant to include intact molecules as well as fragments which retain their ability to bind antigen (e.g., Fab and $F(ab')_2$ fragments). These fragments are typically produced by proteolytically cleaving intact antibodies using enzymes such a papain (to produce Fab fragments) or pepsin (to produce $F(ab')_2$ fragments). The term "antibody" also refers to both monoclonal antibodies and polyclonal antibodies. Polyclonal antibodies are derived from the sera of animals immunized with the antigen. Monoclonal antibodies can be prepared using hybridoma technology (Kohler, et al., *Nature* 256:495 (1975); Hammerling, et al., in *Monoclonal Antibodies and T-Cell Hybridomas*, Elsevier, N.Y. pp. 563-681 (1981)). In general, this technology involves immunizing an animal, usually a mouse, with antigen. The splenocytes of the immunized animals are extracted and fused with suitable myeloma cells, e.g., $SP_2O$ cells. After fusion, the resulting hybridoma cells are selectively maintained in HAT medium and then cloned by limiting dilution (Wands, et al., *Gastroenterology* 80:225-232 (1981)). The cells obtained through such selection are then assayed to identify clones which secrete antibodies that bind to phosphorylated forms of H3 histone, but not to non-phosphorylated forms.

The antibodies, or fragments of antibodies, of the present invention may be used in assays for determining the extent to which phosphorylation of histone has occurred. These assays may be performed either in vitro or they can be performed on cells after they have been lysed. Standard radioimmunoassays or immunometric assays, also known as "two-site" or "sandwich" assays (see Chard, in *Laboratory Techniques in Biochemistry and Molecular Biology*, North Holland Publishing Co., NY (1978)) may be used. In a typical immunometric assay, a quantity of unlabeled antibody is bound to a solid support that is insoluble in the fluid being tested. After the initial binding of antigen to immobilized antibody, a quantity of detectably labeled second antibody (which may or may not be the same as the first) is added to permit detection and/or quantitation of bound antigen (see, e.g., *Radioimmune Assay Methods*, Kirkham, et al., pp. 199-206, E&S Livingstone, Edinburgh (1970)). Many variations of these types of assays are known in the art and may be employed for detection of phosphorylated H3 histone.

Antibodies to phosphorylated histone H3 may also be used in the purification of the protein, (e.g., prior to the counting of radioactivity). For example, antibody may be immobilized on a chromatographic matrix, such as Sepharose 4B (see, e.g., Dean, et al., *Affinity Chromatography, A Practical Approach*, IRLP Press (1986)). The matrix is packed into a column and the preparation containing phosphorylated histone H3 is passed through under conditions that promote binding, e.g., under conditions of low salt. The column is then washed and bound histone is then eluted using a buffer that promotes dissociation from antibody (e.g., a buffer having an altered pH or salt concentration). Alternatively, antibodies specific for phosphorylated H3 histone may be used in Western blots or in immunofluorescence microscopy designed to detect this protein. Again, standard methodology may be employed for these types of assays.

III. Other Methods

Assays for determining if a test compound inhibits the kinase activity of haspin may be performed by incubating haspin and H3 (or a peptide or protein having the H3 site of phosphorylation) with $^{32}P$-ATP both in the presence and absence of a test compound. A reduction in phosphorylation observed in the presence of test compound is an indication that the compound is acting as an inhibitor.

A procedure for increasing haspin activity may be of interest in producing cells that exhibit abnormal mitotic activity and which can therefore be used to look for therapeutic agents or in the study of cell division. Increased phosphorylation of H3 by haspin can be achieved by incorporating nucleotides encoding haspin into an expression vector (e.g., as described in the Examples section). The vector can then be used to transfect cells and the presence of recombinant haspin can be confirmed using standard methodology, e.g., PCR amplification. Since it has been found that a high level expression of haspin is incompatible with cell growth, expression vectors must contain an inducible promoter. Thus, after transfection, the cells are allowed to grow without induction and the effect of increased haspin production is studied by introducing an inducer into cultures. An example using the vector pTRE2pur and the inducer doxycycline is described in the Examples section. In order to determine the effect of test compounds, they may be introduced into cells shortly before induction.

Assays of haspin activity or H3 phosphorylation in biological samples will be of value in examining samples in which cells are undergoing abnormal mitosis (e.g., a tumor sample). These assays can be used to determine whether abnormalities in haspin activity are contributing to the abnormalities in cell division observed. Comparisons may be based upon control samples containing cells that are free of abnormal cells or with results that have been derived from the general population.

IV. Uses of Compositions and Methods

The various compositions and methods described herein will be of use as tools to scientists that are studying cell division and how abnormalities in mitosis contribute to diseases such as cancer. Compounds that alter haspin activity also have potential use as therapeutic agents. Treatments based upon the inhibition of other protein kinases are among the most promising anti-cancer therapies now under investigation and two such inhibitors have already made it to the market, Gleevec for chronic myelogenous leukemia, and Iressa for lung cancer.

EXAMPLES

Example 1

Phosphorylation of Histone H3 by Haspin

This example demonstrates that phosphorylation of threonine-3 in histone H3 occurs during mitosis and that the major kinase responsible for this modification in cultured cells is haspin. Overexpression and RNA interference experiments show that haspin is required for normal mitotic chromosome alignment. Consistent with this function, haspin associates with chromatin and spindle components and is phosphorylated during mitosis.

I. Material and Methods

Antibodies, Proteins, Peptides and Cells

A rabbit anti-serum to a KLH-conjugated peptide corresponding to residues 329-44 of human haspin ([C]DRLER-TRSSRKSKHQE, (SEQ ID NO:15)) was generated and affinity purified on the immunizing peptide by Zymed Laboratories Inc. (South San Francisco, Calif.). The rabbit polyclonal antiserum B8634 to phospho-histone H3 (Thr-3) was produced by immunization with the peptide AR[pT]KQTAR (Ahx)C (SEQ ID NO:16) conjugated to BSA (Ahx=aminohexanoic acid), depleted using the equivalent non-phosphorylated peptide and affinity purified on the phosphorylated peptide (Biosource, Hopkinton, Mass.). Alternatively, rabbit polyclonal antibody to phosphohistone H3 (Thr-3) from Upstate (Lake Placid, N.Y.) may be used with similar results. Rabbit anti-phospho-histone H3 (Ser-28) is from Upstate, rabbit polyclonal and mouse monoclonal anti-phospho-histone H3 (Ser-10) from Cell Signaling Technology and rabbit anti-histone H3 from Abcam (Cambridge, UK). Goat anti-B23/nucleophosmin and mouse 9E10 anti-myc-FITC are from Santa Cruz Biotechnology (Santa Cruz, Calif.) and human autoantibody to centromeres from Immunovision (Springdale, Ariz.).

Mouse monoclonal antibodies to human cyclin A, cyclin B and PCNA are from BD Transduction Laboratories and to alpha-tubulin from Sigma (St Louis, Mo.). Purified calf thymus histones are from Roche. Human histone H3 peptides H3(1-8), H3(1-8)pT3, H3(9-16)pT11 and H3(20-27)pT22 each with an additional Ahx and cysteine residue (≈95% pure) are synthesized by Biosource. Other peptides are human H3 residues 1-21 followed by GGK-biotin and asymmetrically dimethylated at Arg-2 (>95% pure, synthesized by Abgent, San Diego, Calif.), dimethylated at Lys-4 or Lys-9, acetylated at Lys-9 and Lys-14, or phosphorylated at Ser-10 (>90% pure, Upstate). Human HEK293, HeLa and U2OS cells are maintained in 10% FBS/DMEM.

Recombinant Protein Production

Recombinant *Xenopus* H3, tailless H3 (gH3), H2B and H4 histones are prepared according to Luger, et al., *J. Mol. Biol.* 272:301-311 (1997)). To generate plasmids encoding histone tail-GST proteins, PCR products encoding residues 1-45 of human H3 (NM_003537) or 1-26 of human H4 (NM_003541) amplified from the plasmids pBOS-H3-N-GFP and pBOS-H4-N-GFP (Kimura, et al., *J. Cell Biol.* 153:1341-1353 (2001)) and a PCR product encoding residues 1-35 of H2B (NM_003526) amplified from human HeLa cell genomic DNA are inserted into the Nco I site of pETGEX-CT (Sharrocks, *Gene* 138:105-108 (1994)). Site-directed mutants of H3-GST are generated by PCR mutagenesis. A construct encoding the 6His-tagged kinase domain is generated by insertion of a PCR product encoding residues 471-798 of human haspin into the PshA I site of the vector pET45b (+) (Novagen). An equivalent construct containing the mutation K511A is produced by PCR-based mutagenesis. All constructs were confirmed by DNA sequencing and introduced into *E. coli* strain BL21 (Novagen). GST and 6His fusion proteins were purified from IPTG-induced *E. coli* by standard procedures.

Haspin Expression in Mammalian Cells

Using customized double stranded adapters, full length human haspin cDNA (amino acids 1-798, Higgins, *Gene* 267:55-69 (2001)) was ligated into the Hind III-Xba I sites of the expression vector pcDNA3 (Invitrogen) and, to generate myc-tagged haspin, cDNA encoding residues 2-798 was inserted into the pcDNA3-derived plasmid pCANmyc1. To generate a plasmid encoding EGFP-haspin, haspin cDNA encoding amino acids 2-798 is inserted into the Sac II-BamH I sites of pEGFP-C1 (Clontech). To generate inducible vectors, cDNA encoding myc-haspin from pCANmyc-haspin (Hind III-EcoR V) is blunt-ended and inserted into the Pvu II site of pTRE2/pur (BD Clontech) and Nhe I-Xba I fragments encoding EGFP-haspin or EGFP alone from pEGFP-haspin or pEGFP-C1, respectively are ligated into the Nhe I site of pTRE2pur. All constructs are verified by DNA sequencing. Transient transfection is carried out using Lipofectamine 2000 (Invitrogen). Stable transfection of HeLa Tet-On (BD Clontech) cells is carried out using Lipofectin with Plus Reagent (Invitrogen). After 24 h, cells are transferred to 96-well plates and incubated in medium containing 1 µg/ml puromycin and 100 µg/ml G418. Clones expressing myc-haspin or EGFP-haspin in the presence, but not absence, of 1 µg/ml doxycycline are selected by anti-myc immunoblotting or flow cytometric analysis of EGFP fluorescence respectively.

Fluorescence Microscopy

For immunofluorescence, cells or metaphase spreads are fixed with 4% paraformaldehyde/PBS for 10 min, incubated in methanol for 5 min at −20° C., washed 3 times with 5% FBS/PBS over 30 min, then incubated with 2 µg/ml anti-myc 9E10-FITC, 1 µg/ml goat anti-B23/nucleophosmin, 0.1 µg/ml mouse anti-alpha-tubulin, 1/4000 human anti-centromere, 1/1000 mouse anti-phospho-histone H3 (Ser-10) or 0.2 µg/ml rabbit anti-phospho-histone H3 (Thr-3) in 5% FBS/ PBS for 2 h at 25° C. followed by approximately 1 µg/ml donkey anti-goat, mouse or human IgG-Cy3 (Jackson ImmunoResearch) or goat anti-rabbit or mouse IgG-Alexa488 (Invitrogen). To detect DNA 0.5 µg/ml Hoechst 33342 (Sigma) or 2.5 µM DRAQ5 (Alexis) is used. Fluorescence microscopy is carried out using a Nikon TE2000 inverted confocal microscope and video microscopy using a Nikon ECLIPSE E600 inverted fluorescence microscope, with heated stages at 37° C. for live cell imaging.

Cell Synchronization

Where necessary, HeLa Tet-On stable transfectants are incubated with 1 µg/ml doxycycline for 24-48 h prior to synchronization. Cells are synchronized at the G1/S boundary by double thymidine block (Spector, et al., Cells. A Laboratory Manual, Cold Spring Harbor Laboratory Press, Plainview, N.Y. (1997)), or in prometaphase by treatment with 50 ng/ml (HeLa) or 150 ng/ml (NIH3T3) nocodazole or 100 ng/ml colcemid for 12-16 h. For cell cycle analysis, cells are permeabilized in 70% ice-cold ethanol, blocked with 1% BSA/5% FBS and stained with 10 µg/ml mouse monoclonal MPM-2-FSE (Upstate) (Taylor, et al., Cell 89:727-735 (1997)) followed by incubation in 50 µg/ml propidium iodide, 100 U/ml RNAse A, PBS for 1 h at 25° C. to stain DNA. Analysis is conducted on a FACSort flow cytometer (BD Biosciences).

Immunoprecipitation, GST "Pulldown" and Immunoblotting

For immunoprecipitation, cells are suspended in 50 mM Tris/0.5 M NaCl/1% Triton X-100/1% DOC/0.1% SDS/2 mM EDTA, pH 7.4 (buffer L) with 1 µg/ml pepstatin/1 µg/ml leupeptin/1 µg/ml antipain/1 µg/ml chymostatin/1 mM phenylmethylsulphyl fluoride/1 mM NaF/0.1 µM okadaic acid and lysed by shearing 15 times through a 21 gauge needle. Insoluble material is removed by centrifugation for 15 min at 13,000 rpm and the lysates precleared with protein G-Sepharose and concentrations equalized based on Bradford assay (Bio-Rad). Lysates are incubated with antibodies for 1.5 h at 4° C. before addition of protein G-Sepharose for a further 1.5 h. Beads are washed 4 times with buffer L and thrice with Hepes-buffered saline, pH 7.4 (HBS). For GST pulldown assays, cells are lysed in 20 mM Tris/1% Triton X-100/1 mM EDTA/1 mM DTT, pH 7.4 (buffer T) containing 0.3 M NaCl and protease and phosphatase inhibitors as above, clarified, and precleared with glutathione-Sepharose. Cell lysates (200 µg) are incubated in 200 µl buffer T containing 0.4 M NaCl for 1 h at 4° C. with 2.5 µg GST fusion protein pre-absorbed to 5 µl glutathione-Sepharose, followed by three washes in the same buffer. Whole cell lysates for immunoblotting are prepared in 30 mM Tris/1.5% SDS/5% glycerol/0.1% bromophenol blue, pH 6.8. Hypotonic lysis in 10 mM Hepes/0.5% Triton X-100/1.5 mM MgCl$_2$/10 mM KCl, pH 7.4 with protease inhibitors is used to produce nuclear (pellet) and cytoplasm-enriched (supernatant) cell fractions. SDS-PAGE and immunoblotting are carried out using standard procedures (Coligan, et al., Current Protocols in Immunology In Current Protocols (ed. R. Coico). John Wiley & Sons, Inc., New York (1994)). Peptide slot blots to 0.2 µm PVDF Immunblot membrane are carried out with the Bio-Dot SF apparatus (Bio-Rad Laboratories).

In Vitro Kinase Assays

Haspin and aurora B kinase assays are conducted in 30 µl HBS/10 mM MnCl$_2$ with 2.5 µM ATP and 2.5 µCi [gamma $^{32}$P]-ATP (3000 Ci/mmol) or with 100 µM ATP for 15 min at 37° C. Exogenous substrates are added at 0.5-1 µg per reaction for histone and GST proteins and at 0.02 to 1 nmol for peptides. Biotinylated peptides are quantified by HABA/avidin assay (Sigma). Incorporation of $^{32}$P into histone and GST proteins is visualized by SDS-PAGE and autoradiography, and into biotinylated peptides by immobilization on SAM$^2$ Biotin Capture Membrane according the manufacturer's recommendations (Promega Corporation, Madison, Wis.) and Cherenkov counting.

Phosphatase Treatment

Myc-haspin immunoprecipitates from colcemid-treated or untreated induced HeLa Tet-On/myc-haspin cells are incubated with 200 U lambda phosphatase in lambda phosphatase buffer (New England Biolabs) or in buffer alone for 30 min at 30° C. before analysis by SDS-PAGE and immunoblotting.

RNA Interference

Human haspin validated siRNA (ID#1093), murine haspin pre-designed siRNA (ID#67120) and negative control #1 or #2 siRNAs (#4611, 4613) are from Ambion, and human haspin and negative control SMARTpool siRNAs are from Dharmacon. Transfection with siRNAs was carried out with siPORT lipid according to the manufacturer's recommendations (Ambion).

II. Results

Subcellular Localization of Haspin

To determine the subcellular localization of haspin, HeLa cells were transfected with myc-tagged human haspin and anti-myc immunofluorescence staining was performed. The results indicated that myc-haspin is found exclusively in the nucleus during interphase. More intense staining was evident surrounding sub-nuclear structures. A similar haspin pattern has been reported previously in transfected HEK293 and COS cells, although the identity of the compartment was not determined (Tanaka, et al., J. Biol. Chem. 274:17049-17057 (1999); Tanaka, et al., Mol. Hum. Reprod. 7:211-218 (2001)). Double staining with anti-myc and antibodies to B23/nucleophosmin demonstrated that these structures are the nucleoli. Live cell confocal fluorescence microscopy at 37° C. of HeLa cells transfected with EGFP-haspin confirmed that haspin was localized to the nucleus in a pattern similar to that of DNA. The accumulation at perinucleolar regions is not as clear as that seen in fixed cells, suggesting that fixation preferentially stabilizes nucleolar haspin.

In fixed mitotic cells, myc-haspin and EGFP-haspin were found associated with the condensed chromosomes in prophase through anaphase. In metaphase spreads, myc-haspin was found on chromosome arms, with the most intense staining at centromeric regions. When live HeLa cells are visualized at 37° C. by video microscopy, EGFP-haspin is present on the condensing chromosomes in prophase, and remains associated with the condensed chromosomes throughout mitosis. Haspin localization was examined in more detail by confocal microscopy of live mitotic cells. In addition to the localization of EGFP-haspin on chromosomes, it also appeared at centrosomes in prometaphase through telophase. Weaker localization of EGFP-haspin to spindle fibers emanating from the centrosome was apparent from metaphase on, as was localization of EGFP-haspin to the midbody of telophase cells. The localization of EGFP-haspin and alpha-tubulin in fixed cells confirmed that haspin was associated with spindle poles. EGFP alone was found exclusively in the cytoplasm of mitotic cells.

The localization of untagged haspin was assessed using an affinity-purified polyclonal antibody to a peptide representing human haspin amino acids 329-344. By immunoblotting, the antibody was specific for haspin in transfected HEK293 cells and HeLa cells, but did not appear to detect endogenous haspin. Upon fractionation of transfected cells into nucleus and cytoplasm-enriched fractions by hypotonic lysis, haspin was found only in the nuclear fraction. Immunofluorescence of transfected untagged haspin in HeLa cells with this antibody confirmed nuclear localization in interphase, and chromosomal association during mitosis. Although EGFP-haspin can be detected at the centrosome in fixed cells, we have so far been unable to establish a fixation technique that allows immunostaining of haspin or myc-haspin at the spindle or centrosome.

Haspin is a Histone H3 Kinase

The in vitro kinase activity of haspin was also examined. For these experiments we prepared a control haspin protein (myc-haspin-KD) containing a mutation of a single conserved lysine residue (K511A) that is critical for activity in essentially all protein kinases. Immunoprecipitates from vector alone, myc-haspin and myc-haspin-KD transfected HEK293 cell lysates were subjected to in vitro kinase assays in the presence of gamma $^{32}$P-ATP. While no phosphorylated proteins were generated in assays of vector-transfected cells, a radiolabeled band of approximately 85 kDa was visible in myc-haspin immunoprecipitates. This band coincided with the position of myc-haspin detected by immunoblotting, suggesting that myc-haspin had undergone autophosphorylation. No such phosphorylation was apparent when myc-haspin-KD immunoprecipitates were examined, providing evidence that the kinase activity observed is intrinsic to the haspin kinase domain.

Importantly, in the in vitro kinase assays with myc-haspin immunoprecipitates from both HEK293 and HeLa cells, we observed an additional phosphorylated band of approximately 17 kDa. One possibility was that this was a protein directly immunoprecipitated by the anti-haspin antibody due to cross-reactivity. Similar results were obtained, however, when myc-haspin was immunoprecipitated with an anti-myc tag monoclonal antibody, indicating that this was not the case. We reasoned that the 17 kDa protein might be a phosphorylation substrate that co-immunoprecipitates with haspin.

Recognizing the chromosomal location of haspin during mitosis, and that the core histones are major cellular components that have molecular masses in the range of 14-17 kDa, we sought to determine if histones could serve as exogenous substrates for haspin. Strikingly, when a purified mixture of histones H1, H3, H2B, H2A and H4 was tested, haspin showed selectivity for a single band of approximately 17 kDa, remarkably similar in size to the endogenous phosphorylated band. No such band was obtained from in vitro kinase assays of myc-haspin-KD or vector only transfected cells. Based on an overlay of the autoradiogram with the Coomassie Blue stained SDS-PAGE gel, the phosphorylated band appeared to coincide with histone H3.

When purified histones were tested separately as targets for haspin kinase activity, we confirmed that histone H3 was the most efficiently phosphorylated, although in this situation weaker phosphorylation of other histones was also observed. Recombinant histone H3 produced in *E. coli* and lacking post-translational modifications (Luger, et al., *J. Mol. Biol.* 272:301-311 (1997)) was also an efficient substrate for haspin activity, indicating that pre-existing histone modifications are not a requirement for haspin action in vitro. A recombinant form of histone H3 lacking the N-terminal 26 "tail" residues (gH3) was not phosphorylated by haspin, suggesting that the phosphorylation site resides within this region. Recombinant histones H2B and H4 were relatively poor substrates of haspin. We conclude that histone H3 can associate with and serve as a substrate for the haspin kinase, at least in vitro.

Haspin Phosphorylates Histone H3 at Threonine-3

The N-terminal tail regions of the histones are exposed in nucleosomal oligomers and are the major targets of the histone modifications so far analyzed (Jenuwein, et al., *Science* 293:1074-1080 (2001); Turner, *Cell* 111:285-291 (2002)). To determine if haspin targets a residue in the N-terminal tail of H3, we generated a protein (H3-GST) containing the first 45 residues of H3 fused to the N-terminus of GST to preserve the normal orientation of the tail. Immunoprecipitates of myc-haspin from transfected cells were able to phosphorylate H3-GST but not GST alone, nor H2B-GST or H4-GST. To identify residues within the tail that are required for phosphorylation by haspin, we generated H3-GST proteins containing mutations to alanine of each of the 7 serine and threonine residues present (T3A, T6A, S10A, T11A, T22A, S28A, T32A). The mutation T3A abolished phosphorylation by haspin, while the other mutant H3-GSTs behaved as wild-type, suggesting that threonine-3 is the target of phosphorylation by haspin or that it is required for association of haspin with H3-GST.

To examine the interaction of haspin with H3, we utilized the H3-GST fusion proteins in "pulldown" assays from lysates of myc-haspin-transfected cells. In the conditions of the assay, myc-haspin bound to H3-GST, whereas the binding of myc-haspin to GST alone, H2B-GST and H4-GST was not detected. Importantly, the binding of H3-T3A-GST to myc-haspin was indistinguishable from wild-type, indicating that the failure of haspin to phosphorylate this mutant is not due to a failure of the two proteins to associate. Mutation of residues adjacent to threonine-3 (R2A and K4A) abolished detectable association of haspin with H3-GST and substantially reduced phosphorylation of H3-GST by haspin, indicating that these residues are involved in the interaction of haspin and histone H3.

To directly confirm that haspin phosphorylates threonine-3 we generated anti-phospho-histone H3 (Thr-3) antibodies (see Materials and Methods). First, to confirm the specificity of the antibodies we demonstrated that they recognized a synthetic peptide representing residues 1 to 8 of the H3 tail when phosphorylated at threonine-3 but failed to bind to the equivalent non-phosphorylated peptide and to H3 peptides phosphorylated at threonine-11 or -22. Second, we produced a purified recombinant form of the kinase domain of human haspin as a 6His-tagged fusion protein in *E. coli* and an equivalent protein containing the K511A mutation that is kinase-deficient. We then carried out in vitro kinase reactions with a variety of purified substrates and used immunoblotting with anti-phospho-histone H3 (Thr-3) antibodies to detect phosphorylation of threonine-3. The kinase domain of haspin, but not the kinase-KD form, was able to phosphorylate threonine-3 in recombinant histone H3 and in H3-GST. No such phosphorylation was detected on the H3-T3A-GST mutant or on GST alone. Together, these results reveal that both full-length haspin immunoprecipitated from transfected cells and the purified recombinant kinase domain of haspin specifically associate with and phosphorylate a novel residue within the tail of histone H3, threonine-3, at least in vitro.

Histone H3 is Phosphorylated on Threonine-3 During Mitosis

We next wished to determine whether histone H3 is phosphorylated on threonine-3 in cultured cells and, if so, where and when. Prior to these studies, we further characterized recognition by the anti-phospho-histone H3 (Thr-3) antibodies of a variety of H3 peptides carrying other known modifications. This was important because the binding of other phospho-specific H3 antibodies is altered by the presence of flanking modifications (Turner, *Cell* 111:285-291 (2002); Clayton, et al., *FEBS Lett.* 546:51-58 (2003)). We tested biotinylated peptides representing residues 1 to 21 of H3 carrying no modifications, asymmetric dimethylation on arginine-2, dimethylation on lysine-4 or -9, acetylation on lysines-9 and -14, or phosphorylation on serine-10. All the peptides were similarly phosphorylated by the recombinant haspin kinase domain when the incorporation of radiolabeled phosphate from $\gamma^{32}$P-ATP was assessed. In contrast, when the extent of peptide phosphorylation was determined by immunoblotting with the anti-phospho-histone H3 (Thr-3) antibody it was clear that, alone among the tested modifications, methylation of arginine-2 substantially reduced, but did not eliminate, the recognition of phosphorylated threonine-3. Similar results were obtained with two independent affinity-purified anti-phospho-histone H3 (Thr-3) antisera (see Materials and Methods).

To determine the timing of H3 threonine-3 phosphorylation, we synchronized HeLa cells at the G1/S boundary by double thymidine treatment and used the anti-phospho-histone H3 (Thr-3) antibody in immunoblot analysis of cell lysates at various times following release of the block. DNA content analysis was used to follow cell cycle progression and the mitotic index was determined by staining with the antibody MPM-2 as described (Taylor, et al., *Cell* 89:727-35 (1997)). MPM-2 recognizes a group of proteins that are phosphorylated in prophase, prometaphase and metaphase, and dephosphorylated during anaphase (Vandre, et al., *J. Cell Sci.* 94:245-258 (1989)). As expected, phosphorylation of H3 on serine-10 and serine-28 correlated well with the number of mitotic cells. Phosphorylation of H3 on threonine-3 showed a very similar pattern suggesting that this modification, like that of serine-10 and -28, occurs primarily during mitosis.

We next examined the location and timing of H3 threonine-3 phosphorylation in HeLa cells by confocal immunofluorescence microscopy, and compared it to that of serine-10 phosphorylation. Little staining with anti-phospho-histone H3 (Thr-3) antibodies was observed in the majority of interphase cells. Nevertheless, threonine-3 phosphorylation could be detected in a subset of cells without clear chromosome condensation. These cells were identical to those in which serine-10 phosphorylation could first be detected, presumably late G2 cells as previously reported (Hendzel, et al., *Chromosoma* 106:348-360 (1997); Van Hooser, et al., *J. Cell Sci.* 111:3497-3506 (1998)). In prophase, phosphorylated threonine-3 was detected on condensing chromosomes, and prometaphase and metaphase chromosomes were strongly reactive with the antibody. The intensity of staining declined substantially during anaphase and was absent on decondensing chromosomes in telophase.

Overall, the timing of threonine-3 phosphorylation and dephosphorylation was very similar to that of serine-10. In contrast, there were differences in the location of the two modifications. In late G2 cells threonine-3 phosphorylation appeared in a speckled pattern, whereas diffuse patches of serine-10 phosphorylation frequently originating at the nuclear periphery were observed. The puncta of threonine-3 phosphorylation did not coincide with centromeres, suggesting that the modification originates at foci on chromosome arms. By late prophase the two modifications were partially overlapping and had spread over the majority of each chromosome, but the most intense staining for each modification was in distinct locations. Co-staining with centromere antibodies in fixed cells and on spread metaphase chromosomes indicated that, from late prophase on, threonine-3 phosphorylation was strongest between the centromeres, while that of serine-10 was most intense at distinct bands on the chromosome arms. Similar results were obtained in U20S cells, although in this case phosphorylation of H3 at serine-10 and threonine-3 was observed only after chromosome condensation was apparent. It is possible that changes in other histone modifications, particularly at arginine-2, influence the staining pattern observed with phospho-H3 (Thr-3) antibodies. Nevertheless, the most straightforward interpretation is that histone H3 is phosphorylated on threonine-3 during the initial stages of mitosis and dephosphorylated during anaphase.

Haspin Overexpression Causes Increased H3 Threonine-3 Phosphorylation and a Delay During Mitosis As a means to determine its function, we attempted to generate stable HeLa cell lines overexpressing haspin. Despite the ease with which we obtained stable transfectants with vector alone, stable clones from cells transfected with haspin all contained undetectable or aberrantly-sized haspin proteins. This suggested that high-level haspin expression is incompatible with cell growth. To circumvent this problem, we generated stable transfectants of HeLa Tet-On cells (BD Clontech) with myc-haspin cDNA in the vector pTRE2pur and with vector alone as a control. In this system, the haspin gene is under an inducible promoter and is not expressed unless doxycycline is added. We obtained stable lines that express levels of myc-haspin undetectable by immunoblotting prior to induction, and maximal levels after 24 h treatment with 1 µg/ml doxycycline.

After induction, cells expressing myc-haspin showed a deficit in proliferation compared with uninduced cells (cell number reduced to 58% and 60% of uninduced control after 8 days in two separate experiments). Doxycycline had no such effect on the growth of cells transfected with vector alone (cell numbers were 104% and 115% of uninduced control after 8 days in two experiments). We then used DNA content analysis and MPM-2 staining to compare progression through the cell cycle of synchronized populations of myc-haspin and vector-transfected cells in inducing conditions. After release from a double thymidine block at G1/S, both myc-haspin and control cells progressed through S phase and entered G2 with similar kinetics. Although entry into mitosis as defined by MPM-2 staining was similar in the two cell lines, the disappearance of the MPM-2 epitope was markedly delayed in myc-haspin expressing cells, indicating a delay prior to anaphase. A similar effect was seen when induced and uninduced myc-haspin transfected cells were compared, while doxycycline treatment of vector-transfected cells had no effect on cell cycle progression. It is unlikely that the kinase activity of haspin directly induces the MPM-2 phospho-epitope because no increase in the intensity of MPM-2 staining was observed in haspin-transfected cells, and the extended period of mitosis was also reflected in a delay in exit from G2/M and entry into G1 as determined by DNA content. Furthermore, in a separate experiment, enumeration of mitotic cells at 13 h following release revealed an accumulation in prophase/prometaphase and a corresponding decrease in the number of anaphase/telophase cells upon overexpression of myc-haspin.

Immunoblotting of lysates from synchronized cells showed that myc-haspin protein was present at similar levels throughout the cell cycle. Interestingly however, the mobility of myc-haspin was significantly retarded at time points during which cells were undergoing mitosis, particularly at 11 to 14 h post release. In fact, myc-haspin in lysates of mitotic cells isolated by selective detachment, or after colcemid treatment, was almost entirely in this larger form. Myc-haspin returned to a size of approximately 85 kDa after release of cells from the mitotic block and only this lower form was detected in interphase cells. Treatment of myc-haspin immunoprecipitated from colcemid-blocked cells with lambda phosphatase showed that the increase in size during mitosis could be ascribed to phosphorylation. We conclude that haspin is strongly phosphorylated during mitosis.

To examine the kinase activity of overexpressed haspin through the cell cycle, we immunoprecipitated myc-haspin from the synchronized cell lysates and conducted in vitro kinase assays using H3-GST as a substrate, or H3-T3A-GST as a negative control. Despite the clear phosphorylation of myc-haspin during mitosis, no change in its kinase activity was seen during the cell cycle. Consistent with this, we saw no difference in the activity of myc-haspin immunoprecipitated from mitotic cells obtained by selective detachment or colcemid block and interphase or asynchronous cells.

To determine the effect of haspin overexpression on histone phosphorylation, we examined the synchronized cell lysates by immunoblotting with anti-phospho-histone H3 antibodies. In control cells, the phosphorylation of histone H3 on threonine-3, serine-10 and serine-28 correlated well with the number of mitotic cells, as expected. In myc-haspin expressing cells, however, phosphorylation on threonine-3 was dramatically increased and was present throughout the cell cycle. In contrast, the intensity of serine-10 and -28 phosphorylation on H3 was not significantly altered by myc-haspin overexpression. These findings provide strong support for the hypothesis that haspin acts as a histone H3 threonine-3 kinase in vivo.

Endogenous Haspin is Responsible for Histone H3 Threonine-3 Phosphorylation During Mitosis We wished to determine the role of endogenous haspin during mitosis. Although the anti-haspin antibody was unable to detect endogenous haspin in HeLa or HEK-293 cells by immunoblotting, our previous Northern analyses suggested that all proliferating cell lines express haspin mRNA (Higgins, *Gene* 267:55-69 (2001)). As a more sensitive approach to detect endogenous haspin activity, we analyzed anti-haspin immunoprecipitates from untransfected HeLa cells by in vitro kinase assay. This revealed a kinase activity that could phosphorylate H3-GST but not H3-T3A-GST, suggesting the presence of an H3 threonine-3 kinase, most likely endogenous haspin. No such activity was found in negative control immunoprecipitates. The pattern of substrate specificity clearly differed from that of aurora B immunoprecipitated from mitotic HeLa cells, which was able to phosphorylate H3-GST and H3-T3A-GST but not H3-S10A-GST, as expected.

When nocodazole-blocked cells or mitotic cells obtained by selective detachment were compared to an asynchronous or interphase population, no increase in the kinase activity of immunoprecipitated endogenous haspin was seen. Indeed, when we examined endogenous haspin from cells synchronized at G1/S and then released, little change in kinase activity was seen during the cell cycle, confirming the results with overexpressed haspin. In contrast, the activity and protein level of aurora B increased in G2/M as previously reported (Bischoff, et al., *EMBO J.* 17:3052-3065 (1998)). It should be noted, however, that these results do not rule out regulation of haspin activity during mitosis in vivo.

To determine whether endogenous haspin is required for phosphorylation of H3 on threonine-3, we conducted RNA interference. At 100 nM, transfection of small interfering RNA ID#1093 specific for human haspin reduces haspin mRNA levels in HeLa cells by 89%±1% (Ambion). We confirmed that transfection of 20 or 100 nM of this siRNA, but not of a negative control siRNA reduced endogenous haspin kinase activity in both asynchronous and nocodazole-blocked mitotic HeLa cells. The treatment had little effect on the aurora B kinase activity detected in the same cell lysates. Strikingly, haspin siRNA dramatically reduced the phosphorylation of H3 on threonine-3 seen in mitotic cells. In contrast, no change was seen in the level of H3 phosphorylation on serine-10. Haspin siRNA caused a similar reduction in H3 threonine-3 phosphorylation in U2OS cells and, using a different murine haspin siRNA, in NIH3T3 cells. Therefore, endogenous haspin is required for H3 phosphorylation on threonine-3 in mitotic cells.

Depletion of Haspin Prevents Normal Metaphase Chromosome Alignment

To examine the effect of haspin RNA interference on mitosis, we transfected U2OS and HeLa cells with haspin or control siRNAs and assessed the distribution of chromosomes in mitotic cells by immunofluorescence. Among haspin siRNA-transfected U2OS cells we noted an increased number with a late prometaphase configuration in which a partial metaphase plate was present, but many chromosomes were apparently "stranded" near the spindle poles. Staining with anti-centromere antibodies revealed doublets on most of the unaligned chromosomes indicating that they were monoorientated sister chromatid pairs. The centromeres of chromosomes that were present at the metaphase plate often appeared poorly aligned. Enumeration of mitotic cells showed that haspin siRNA caused an accumulation of cells in prometaphase and a corresponding decrease in anaphase and telophase cells compared to controls. We noted that within the haspin siRNA-treated population, H3 threonine-3 phosphorylation was reduced to varying extents in different cells. When we examined only those cells with low levels of threonine-3 phosphorylation ("low pT3"), the increased ratio of prometaphase over metaphase cells was particularly dramatic. In cells with moderate to high levels of pT3, or in control transfectants, there was a 50%-50% split between cells classified as prometaphase and metaphase, and fewer than 10% had a partial metaphase configuration. In contrast, among haspin siRNA transfected cells with low pT3 over 80% were in prometaphase and less than 20% in metaphase. Similar results were obtained with an independent haspin siRNA reagent and in HeLa cells, although these cells apparently required more complete haspin depletion to disrupt mitosis. We conclude that haspin is required for normal alignment of chromosomes at metaphase.

III. Discussion

Haspin is a Mitotic Kinase

The present example shows by a number of criteria that haspin is a mitotic kinase. First and most importantly, haspin overexpression or depletion results in defective mitosis. Second, haspin has a unique pattern of association with critical components of the mitotic machinery. Third, phosphorylation of haspin and haspin-dependent phosphorylation of histone H3 occur specifically during mitosis.

Haspin localizes to condensed chromosomes throughout mitosis, to the centrosomes following nuclear envelope breakdown (NEBD), to spindle microtubules during metaphase and to the midbody in telophase. This localization is similar to that of aurora A and Polo-like kinase 1 (Plk1) except that these proteins are found at the centrosome prior to NEBD and, although Plk1 is found at centromeres, neither show prominent association with mitotic chromosome arms (Cammena, et al., *Rev. Mol. Cell. Biol.* 4:842-854 (2003); Barr, et al., *Nat. Rev. Mol. Cell. Biol.* 5:429-440 (2004)). Like aurora B, haspin can associate with condensing chromosomes, particularly at centromeric regions, and with spindle components. We found no evidence, however, that haspin undergoes the sudden transfer from chromosomes to the spindle typical of chromosome passenger proteins as anaphase begins (Carmena, et al., *Rev. Mol. Cell. Biol.* 4:842-854 (2003)).

Interestingly, we could not detect a change in haspin kinase activity during the cell cycle, consistent with the lack of residues that can be phosphorylated in the potential activation loop of its kinase domain (Higgins, *Prot. Sci.* 10:1677-1684 (2001)). We suspect that mitotic phosphorylation controls haspin function by modulating binding to protein(s) that regulate its activity or by regulating haspin association with proteins that target it to chromatin and the spindle. This type of targeting of aurora B by INCENP and survivin has been well described (Carmena, et al., *Rev. Mol. Cell. Biol.* 4:842-854 (2003)). Such associations may be disrupted in the lysis conditions used in our experiments.

Haspin is Required for Normal Mitosis

We find that haspin depletion by RNA interference prevents normal chromosome alignment at metaphase, while haspin overexpression results in a delay prior to metaphase. In common with other mitotic kinases such as Plk1 and auroras A and B (Carmena, et al., *Rev. Mol. Cell. Biol.* 4:842-854 (2003); Barr, et al., *Nat. Rev. Mol. Cell. Biol.* 5:429-440 (2004)), it appears that haspin activity must be maintained between certain limits and that either too much or too little prevents normal mitosis. The failure of chromosome congression upon reduction of haspin activity is reminiscent of the effect of aurora B depletion (Adams, et al., *J. Cell Biol.* 153: 865-880 (2001); Shannon, et al., *Curr. Biol.* 12:R458-460 (2002); Andrews, et al., *Curr. Opin. Cell Biol.* 15:672-683 (2003)). It is possible that haspin plays a role in correcting syntelic chromosome attachments to the spindle, a normal process during formation of the metaphase plate that is dependent on aurora B (Andrews, et al., *Curr. Opin. Cell Biol.* 15: 672-683 (2003)). We note also that the effect of haspin depletion is similar to that of disrupting the function of centromeric kinesin-related proteins, particularly CENP-E, or of depleting the kinetochore kinase Bub1 (Schaar, et al., *J. Cell Biol.* 139:1373-1382 (1997); Johnson, et al., *J. Cell Sci.* 117: 1577-1589 (2004)). Haspin may therefore play a role in regulating kinetochore assembly and spindle attachment or in modulating the activity of microtubule motors responsible for chromosome movement.

In another functional study of haspin, Tanaka, et al. found that transient transfection of HEK293 cells with murine EGFP-haspin caused a profound decrease in the proportion of cells with G2/M DNA content and an accumulation in those with G1 DNA content after 4 days. A mutated form of haspin that has 10 amino acids deleted from the kinase domain, and lacks kinase activity, caused the same effect after 2 days (Tanaka, et al., *J. Biol. Chem.* 274:17049-17057 (1999)). The basis for the disparity with our results is not known. HEK293 cells are reported to have an ineffective spindle checkpoint (Kung, et al., *Proc. Natl. Acad. Sci. USA* 87:9553-9557 (1990)) so it is possible that haspin-induced mitotic defects lead to subsequent activation of a G1 checkpoint in these cells. Alternatively, haspin might have another role in control of S-phase entry. To fully understand the function of haspin it will be necessary to identify its substrates. We have identified one such substrate as threonine-3 of the core histone H3.

Phosphorylation of Histone H3 at Threonine-3

We show that during mitosis the core histone H3 is phosphorylated at threonine-3. Polioudaki, et al. recently reported comparable results (Polioudaki, et al., *FEBS Lett.* 560:39-44 (2004)), although we extend these findings in two important ways. First we find that the timing of onset of serine-10 and threonine-3 phosphorylation is similar and can be detected prior to clear chromatin condensation in HeLa cells, likely late in G2 (Hendzel, et al., *Chromosoma* 106:348-360 (1997); Van Hooser, et al., *J. Cell Sci.* 111: 3497-3506 (1998)). Second, we carried out co-immunostaining of phosphorylated serine-10 and threonine-3, and show directly that they have distinct localizations during mitosis. Threonine-3 phosphorylation appears to originate at foci in on the chromosome arms. By metaphase, it is most intense at centromeric chromatin and is also present along the chromosome arms, reflecting the distribution of haspin. In contrast, serine-10 phosphorylation was found primarily on chromosome arms in late prophase through metaphase. The two modifications are removed contemporaneously prior to chromosome decondensation in telophase.

The existence of a histone H3 threonine-3 kinase was first described 25 years ago. Shoemaker and Chalkley (Shoemaker, et al., *J. Biol. Chem.* 255:11048-11055 (1980)) characterized a kinase activity associated with bovine thymus chromatin that displayed "extraordinary substrate specificity for histone H3" and phosphorylated threonine-3. More recently, an H3 threonine-3 kinase from avian nuclear envelope-associated peripheral heterochromatin that was able to form a complex with HP1-gamma-GST protein was described (Polioudaki, et al., *FEBS Lett.* 560: 39-44 (2004)). The identity of the kinase, however, was not determined in either study. Four lines of evidence lead us to conclude that haspin is the major kinase responsible for mitotic histone H3 threonine-3 phosphorylation, at least in HeLa, U2OS and NIH3T3 cells. First, overexpression of myc-haspin leads to increased phosphorylation of H3 specifically at threonine-3. Second, small inhibitory RNAs that deplete endogenous haspin activity dramatically reduce mitotic phosphorylation of H3 at threonine-3. Third, haspin associates with mitotic chromosomes at the time that H3 is phosphorylated on threonine-3. Fourth, haspin specifically associates with histone H3 and phosphorylates threonine-3 in vitro. The effects of overexpression and RNAi suggest that haspin is a component of the machinery required for H3 threonine-3 phosphorylation during mitosis. When coupled with the finding that haspin associates with and phosphorylates H3 in vitro, these experiments provide persuasive evidence that haspin directly phosphorylates H3 in vivo.

The function of Mitotic Histone H3 Threonine-3 Phosphorylation

Although haspin siRNA did not prevent chromosome condensation, our results do not rule out a more subtle effect on chromatin structure. The timing of threonine-3 phosphorylation suggests that it could play a role in facilitating condensation and/or resolution of sister chromatids in late G2 and prophase. This might occur through alterations in the recruitment or function of condensins, cohesins or topoisomerases (Swedlow, et al., *Mol. Cell.* 11:557-569 (2003)). Defects in chromatin structure caused by inappropriate threonine-3 phosphorylation might hinder chromosome alignment later in mitosis, particularly given the importance of cohesion for bi-orientation (Tanaka, *Curr. Opin. Cell Biol.* 14:365-371 (2002)). Alternatively, its presence at centromeric regions might reflect a more direct role for threonine-3 phosphorylation in regulating the attachment or activity of spindle microtubules at kinetochores. Tension across paired kinetochores is critical to stabilize attachment of bi-orientated chromosomes to the spindle. It has been proposed that tension pulls kinetochores away from aurora B at the inner centromere, thereby regulating kinase access to its substrates and selectively stabilizing bi-orientated attachments (Tanaka, *Curr. Opin. Cell Biol.* 14:365-371 (2002); Andrews, et al., *Curr. Opin. Cell Biol.* 15:672-683 (2003)). It is possible that phosphorylation of centromeric nucleosomes on threonine-3 of H3 influences transmission of tension between kinetochores and centromeric chromatin. This could affect centromeric separation of sister chromatids and impact chromosome bi-orientation, perhaps by altering aurora B activity.

At the molecular level, threonine-3 phosphorylation might directly influence inter-nucleosomal contacts or could generate a binding site for regulatory proteins during mitosis, in much the same way that Lys-9 methylation facilitates HP1 binding (Lachner, et al., *Curr. Opin. Cell Biol.* 14:286-298 (2002)). Alternatively, it has been hypothesized that threonine-3 serves as a component of a "binary switch." Phosphorylation of threonine-3 could serve to eject as yet undefined proteins bound to the adjacent methylated lysine-4 residue (Fischle, et al., *Nature* 425:475-479 (2003)). Lysine-4 tri- or dimethylation is associated with an active or competent transcriptional state, and a more "open" chromatin structure (Schneider, et al., *Nat. Cell Biol.* 6:73-77 (2004)), which might therefore be counteracted by threonine-3 phosphorylation during mitosis. Arginine-2 in histone H3 can be methylated too (Schurter, et al., *Biochemistry* 40:5747-5756 (2001)) and similar interplay between threonine-3 and this residue could take place.

Crosstalk between non-adjacent histone modifications also occurs (Fischle, et al., *Curr. Opin. Cell Biol.* 15:172-183 (2003)) and phosphorylation of threonine-3 might influence the binding or activity of other histone-modifying enzymes. Prior modifications might also impinge upon the ability of haspin to phosphorylate H3. We find that haspin phosphorylates recombinant H3 and chemically synthesized H3 peptides that lack amino acid modifications, and associates with and phosphorylates recombinant H3-GST. In addition, H3 peptides containing a variety of modifications are equally good substrates for the haspin kinase domain. Together, these results suggest that haspin activity is not influenced by pre-existing H3 modifications in vitro. We cannot rule out, however, the possibility that haspin activity toward certain modified forms of H3 might be increased or decreased in vivo. This might occur because of the presence of combinations of histone modifications not tested in our in vitro study, the existence of other proteins in vivo that might compete for binding to modified H3, and the influence of the N-domain of haspin that was not present in the recombinant haspin protein we used. Indeed, the association of full-length haspin with H3-GST is reduced by mutations at arginine-2 and lysine-4.

Non-Histone Targets of Haspin Activity

It should be noted that it is unlikely that the sole target of haspin activity is histone H3 and therefore we cannot ascribe the effects of manipulating haspin activity only to its influence on H3 threonine-3 phosphorylation. The presence of haspin at centrosomes and the spindle during mitosis strongly indicates that substrates will be found at these locations too. In fact, we have identified mitotic spindle and centrosomal proteins as potential haspin-binding proteins in a yeast two-hybrid screen and we have noted spindle disruptions in mitosis following haspin siRNA treatment. Haspin therefore has features in common with members of the Aurora, Nek and Polo families that regulate the activity of both chromatin and spindle proteins at multiple stages of mitosis (Nigg, *Nat. Rev. Mol. Cell. Biol.* 2:21-32 (2001)). Indeed, the overlap in haspin, Aurora and Polo functions and localization suggest that it will be productive to investigate interactions between haspin and these other kinases.

IV. Conclusion

To the best of our knowledge, an equivalent of threonine-3 is found in histone H3 of all eukaryotes, suggesting a highly conserved and critical function for this residue. Furthermore, the presence of haspin genes in diverse eukaryotes is suggestive of a crucial function in eukaryotic life (Higgins, *Cell. Mol. Life. Sci.* 60:446-62 (2003)). The limited information available regarding the two haspin homologues in budding yeast is consistent with the function of haspin that we describe. The mRNA levels of haspin homologue ALK1 are strikingly periodic during the mitotic cell cycle, with a peak in expression early in mitosis (Cho, et al., *Mol. Cell.* 2:65-73 (1998); Spellman, et al., *Mol. Biol. Cell* 9:3273-3297 (1998)). The second homologue, YBL009W, is significantly induced during sporulation (Chu, et al., *Science* 282:699-705 (1998)). The data suggest that Alk1p and Yb1009wp function during mitosis and meiosis respectively (Higgins, *Cell. Mol. Life. Sci.* 60:446-462 (2003)). We propose that haspin is a member of the select group of kinases with a critical role in integrating the regulation of chromosome and spindle function during mitosis and probably meiosis. The high level of haspin in post-meiotic spermatids (Tanaka, et al., *J. Biol. Chem.* 274: 17049-17057 (1999)) also might suggest a role in the dramatic reorganization and compaction of chromatin that occurs during spermiogenesis. Further study of haspin function will help decipher the histone code and is likely to provide crucial insight into the mechanisms that maintain genomic stability during mitotic and meiotic cell division.

Example 2

Microtiter Plate Haspin Kinase Assay

To demonstrate the potential use of phosphohistone-H3 (Thr-3) antibodies in a high-throughput format, we have conducted pilot experiments of an ELISA-based haspin kinase assay. In these assays, H3-GST substrate protein (or H3-T3A-GST non-phosphorylable control) was immobilized on 96-well microtiter plates by incubation in PBS overnight at 4° C. Following washing and blocking with 1% BSA/TBS, 6His-haspin kinase was added to the wells in 50 μl total volume of Hepes-buffered saline (HBS)/100 μM ATP/10 mM $MnCl_2$ and allowed to phosphorylate the immobilized substrate for 20 min at 37° C. After washing thrice with TBS/0.1% Tween-20, affinity-purified polyclonal anti-phosphohistone H3 (Thr-3) antibodies were added for 1 h at room temperature. After washing, antibody binding (i.e. phosphorylation) was detected using 1/2000 dilution of donkey anti-rabbit IgG-Horse Radish Peroxide (HRP) conjugate (Jackson) followed by tetramethylbenzidine (TMB) color development (BD Biosciences). Measurement of $A_{450\ nm}$-$A_{570\ nm}$ (to correct for well-to-well variation in background absorbance) was carried out after addition of $H_2SO_4$. The results indicated that this assay can sensitively and specifically detect haspin kinase-mediated phosphorylation of H3-GST. Titration of the kinase, substrate and phosphospecific antibody demonstrated that as little as 6 ng/well kinase, 100 ng/well (2.5 pmol/well) substrate and 0.1 μg/ml phosphospecific antibody could be used to generate a clear signal above the background defined by the H3-T3A-GST mutated substrate. These results demonstrate the feasibility of the general approach, and that sufficient quantities of proteins can be produced to allow high throughput screening. Furthermore, using this assay system we have demonstrated inhibition of haspin kinase activity by EDTA and by the peptide H3(1-8) (ARTKQTAR, SEQ ID NO:1).

What is claimed is:

1. A substantially pure polypeptide comprising the amino acid sequence ARTKQ (SEQ ID NO:4), wherein:
   a) said polypeptide is 5-135 amino acids in length;
   b) said polypeptide inhibits the phosphorylation of human histone H3 by haspin;
   c) said polypeptide is not itself histone H3;
   d) said polypeptide optionally includes an additional methionine as the N terminal amino acid; and
   e) said polypeptide is present in a solution that further comprises human haspin (SEQ ID NO:17) and a phosphorylated polypeptide that has an amino acid sequence identical to said polypeptide but in which the threonine in said ARTKQ sequence has been phosphorylated.

2. The substantially pure polypeptide of claim 1, wherein said polypeptide is 8-20 amino acids in length.

3. The substantially pure polypeptide of claim 1, wherein said polypeptide consists of the amino acid sequence ARTKQ (SEQ ID NO:4) and includes an additional methionine as the N terminal amino acid.

4. The substantially pure polypeptide of claim 1, wherein said polypeptide consists of the amino acid sequence ARTKQ (SEQ ID NO:4).

5. The substantially pure polypeptide of claim 1, wherein said polypeptide consists of an amino acid sequence selected from the group consisting of:
   ARTKQTAR (SEQ ID NO:1);
   ARTKQTA (SEQ ID NO:2);
   ARTKQT (SEQ ID NO:3); and
   wherein said polypeptide includes an additional methionine as the N terminal amino acid.

6. The substantially pure polypeptide of claim 1, wherein said polypeptide consists of an amino acid sequence selected from the group consisting of:
   ARTKQTAR (SEQ ID NO:1);
   ARTKQTA (SEQ ID NO:2); and
   ARTKQT (SEQ ID NO:3).

7. A substantially pure peptide consisting of an amino acid sequence selected from the group consisting of:
   AR(pT)KQTAR (SEQ ID NO:8);
   AR(pT)KQTA (SEQ ID NO:9);
   AR(pT)KQT (SEQ ID NO:10);
   AR(pT)KQ; (SEQ ID NO:11);
   R(pT)KQTAR (SEQ ID NO:12);
   R(pT)KQTA (SEQ ID NO:13); and
   R(pT)KQT (SEQ ID NO:14);
   wherein
   a) (pT) represents phosphorylated threonine,
   b) said polypeptide is capable of inducing the generation of antibodies, that bind to phosphorylated human H3 histone, when administered to an animal capable of antibody production, and
   c) said peptide optionally includes an additional methionine as the N terminal amino acid.

8. A substantially pure polypeptide comprising the amino acid sequence RTKQT (SEQ ID NO:7), wherein:
   a) said polypeptide is 5-135 amino acids in length;
   b) said polypeptide inhibits the phosphorylation of human histone H3 by haspin;
   c) said polypeptide is not itself histone H3;
   d) said polypeptide optionally includes an additional methionine as the N terminal amino acid;
   e) said polypeptide is present in a solution that further comprises human haspin (SEQ ID NO:17) and a phosphorylated polypeptide that has an amino acid sequence identical to said polypeptide but in which the threonine in said RTKQT sequence has been phosphorylated.

9. The substantially pure polypeptide of claim 8, wherein said polypeptide consists of the amino acid sequence RTKQT (SEQ ID NO:7).

10. A substantially pure peptide consisting of an amino acid sequence selected from the group consisting of:
    RTKQTAR (SEQ ID NO:5);
    RTKQTA (SEQ ID NO:6); and
    RTKQT (SEQ ID NO:7);
    wherein said peptide optionally includes an additional methionine as the N terminal amino acid.

* * * * *

SEQUENCE LISTING

<160> NUMBER OF SEQ ID NOS: 21

<210> SEQ ID NO 1
<211> LENGTH: 8
<212> TYPE: PRT
<213> ORGANISM: Homo sapiens

<400> SEQUENCE: 1

Ala Arg Thr Lys Gln Thr Ala Arg
1               5

<210> SEQ ID NO 2
<211> LENGTH: 7
<212> TYPE: PRT
<213> ORGANISM: Homo sapiens

<400> SEQUENCE: 2

Ala Arg Thr Lys Gln Thr Ala
1               5

<210> SEQ ID NO 3
<211> LENGTH: 6
<212> TYPE: PRT
<213> ORGANISM: Homo sapiens

<400> SEQUENCE: 3

Ala Arg Thr Lys Gln Thr
1               5

<210> SEQ ID NO 4
<211> LENGTH: 5
<212> TYPE: PRT
<213> ORGANISM: Homo sapiens

<400> SEQUENCE: 4

Ala Arg Thr Lys Gln
1               5

<210> SEQ ID NO 5
<211> LENGTH: 7
<212> TYPE: PRT
<213> ORGANISM: Homo sapiens

<400> SEQUENCE: 5

Arg Thr Lys Gln Thr Ala Arg
1               5

<210> SEQ ID NO 6
<211> LENGTH: 6
<212> TYPE: PRT
<213> ORGANISM: Homo sapiens

<400> SEQUENCE: 6

Arg Thr Lys Gln Thr Ala
1               5

<210> SEQ ID NO 7
<211> LENGTH: 5
<212> TYPE: PRT
<213> ORGANISM: Homo sapiens

<400> SEQUENCE: 7

Arg Thr Lys Gln Thr

```
<210> SEQ ID NO 8
<211> LENGTH: 8
<212> TYPE: PRT
<213> ORGANISM: Homo sapiens

<400> SEQUENCE: 8

Ala Arg Thr Lys Gln Thr Ala Arg
1               5

<210> SEQ ID NO 9
<211> LENGTH: 7
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 9

Ala Arg Thr Lys Gln Thr Ala
1               5

<210> SEQ ID NO 10
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 10

Ala Arg Thr Lys Gln Thr
1               5

<210> SEQ ID NO 11
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 11

Ala Arg Thr Lys Gln
1               5

<210> SEQ ID NO 12
<211> LENGTH: 7
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 12

Arg Thr Lys Gln Thr Ala Arg
1               5

<210> SEQ ID NO 13
<211> LENGTH: 6
<212> TYPE: PRT
<213> ORGANISM: Homo sapiens
<220> FEATURE:
```

```
<221> NAME/KEY: MOD_RES
<222> LOCATION: (3)..(3)
<223> OTHER INFORMATION: PHOSPHORYLATION

<400> SEQUENCE: 13

Arg Thr Lys Gln Thr Ala
1               5

<210> SEQ ID NO 14
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 14

Arg Thr Lys Gln Thr
1               5

<210> SEQ ID NO 15
<211> LENGTH: 17
<212> TYPE: PRT
<213> ORGANISM: Homo sapiens

<400> SEQUENCE: 15

Cys Asp Arg Leu Glu Arg Thr Arg Ser Ser Arg Lys Ser Lys His Gln
1               5                   10                  15

Glu

<210> SEQ ID NO 16
<211> LENGTH: 10
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (9)..(9)
<223> OTHER INFORMATION: Aminohexanoic acid

<400> SEQUENCE: 16

Ala Arg Thr Lys Gln Thr Ala Arg Asn Cys
1               5                   10

<210> SEQ ID NO 17
<211> LENGTH: 798
<212> TYPE: PRT
<213> ORGANISM: Homo sapiens

<400> SEQUENCE: 17

Met Ala Ala Ser Leu Pro Gly Pro Gly Ser Arg Leu Phe Arg Thr Tyr
1               5                   10                  15

Gly Ala Ala Asp Gly Arg Arg Gln Arg Arg Pro Gly Arg Glu Ala Ala
                20                  25                  30

Gln Trp Phe Pro Pro Gln Asp Arg Arg Arg Phe Phe Asn Ser Ser Gly
            35                  40                  45

Ser Ser Asp Ala Ser Ile Gly Asp Pro Ser Gln Ser Asp Asp Pro Asp
        50                  55                  60

Asp Pro Asp Asp Pro Asp Phe Pro Gly Ser Pro Val Arg Arg Arg Arg
65                  70                  75                  80
```

```
Arg Cys Pro Gly Gly Arg Val Pro Lys Asp Arg Pro Ser Leu Thr Val
                85                  90                  95
Thr Pro Lys Arg Trp Lys Leu Arg Ala Arg Pro Ser Leu Thr Val Thr
            100                 105                 110
Pro Arg Arg Leu Gly Leu Arg Ala Arg Pro Gln Lys Cys Ser Thr
            115                 120                 125
Pro Cys Gly Pro Leu Arg Leu Pro Pro Phe Pro Ser Arg Asp Ser Gly
            130                 135                 140
Arg Leu Ser Pro Asp Leu Ser Val Cys Gly Gln Pro Arg Asp Gly Asp
145                 150                 155                 160
Glu Leu Gly Ile Ser Ala Ser Leu Phe Ser Ser Leu Ala Ser Pro Cys
                165                 170                 175
Pro Gly Ser Pro Thr Pro Arg Asp Ser Val Ile Ser Ile Gly Thr Ser
            180                 185                 190
Ala Cys Leu Val Ala Ala Ser Ala Val Pro Ser Asp Leu His Leu Pro
            195                 200                 205
Glu Val Ser Leu Asp Arg Ala Ser Leu Pro Cys Ser Gln Glu Glu Ala
            210                 215                 220
Thr Gly Gly Ala Lys Asp Thr Arg Met Val His Gln Thr Arg Ala Ser
225                 230                 235                 240
Leu Arg Ser Val Leu Phe Gly Leu Met Asn Ser Gly Thr Pro Glu Asp
                245                 250                 255
Ser Glu Phe Arg Ala Asp Gly Lys Asn Met Arg Glu Ser Cys Cys Lys
                260                 265                 270
Arg Lys Leu Val Val Gly Asn Gly Pro Glu Gly Pro Gly Leu Ser Ser
            275                 280                 285
Thr Gly Lys Arg Arg Ala Thr Gly Gln Asp Ser Cys Gln Glu Arg Gly
            290                 295                 300
Leu Gln Glu Ala Val Arg Arg Glu His Gln Glu Ala Ser Val Pro Lys
305                 310                 315                 320
Gly Arg Ile Val Pro Arg Gly Thr Asp Arg Leu Glu Arg Thr Arg Ser
                325                 330                 335
Ser Arg Lys Ser Lys His Gln Glu Ala Thr Glu Thr Ser Leu Leu His
            340                 345                 350
Ser His Arg Phe Lys Lys Gly Gln Lys Leu Gly Lys Asp Ser Phe Pro
            355                 360                 365
Thr Gln Asp Leu Thr Pro Leu Gln Asn Ala Cys Phe Trp Thr Lys Thr
            370                 375                 380
Arg Ala Ser Phe Ser Phe His Lys Lys Lys Ile Val Thr Asp Val Ser
385                 390                 395                 400
Glu Val Cys Ser Ile Tyr Thr Thr Ala Thr Ser Leu Ser Gly Ser Leu
                405                 410                 415
Leu Ser Glu Cys Ser Asn Arg Pro Val Met Asn Arg Thr Ser Gly Ala
            420                 425                 430
Pro Ser Ser Trp His Ser Ser Ser Met Tyr Leu Leu Ser Pro Leu Asn
            435                 440                 445
Thr Leu Ser Ile Ser Asn Lys Lys Ala Ser Asp Ala Glu Lys Val Tyr
            450                 455                 460
Gly Glu Cys Ser Gln Lys Gly Pro Val Pro Phe Ser His Cys Leu Pro
465                 470                 475                 480
Thr Glu Lys Leu Gln Arg Cys Glu Lys Ile Gly Glu Gly Val Phe Gly
                485                 490                 495
Glu Val Phe Gln Thr Ile Ala Asp His Thr Pro Val Ala Ile Lys Ile
```

-continued

```
                500             505             510
Ile Ala Ile Glu Gly Pro Asp Leu Val Asn Gly Ser His Gln Lys Thr
            515                 520                 525
Phe Glu Glu Ile Leu Pro Glu Ile Ile Ile Ser Lys Glu Leu Ser Leu
            530                 535                 540
Leu Ser Gly Glu Val Cys Asn Arg Thr Glu Gly Phe Ile Gly Leu Asn
545                 550                 555                 560
Ser Val His Cys Val Gln Gly Ser Tyr Pro Pro Leu Leu Leu Lys Ala
                565                 570                 575
Trp Asp His Tyr Asn Ser Thr Lys Gly Ser Ala Asn Asp Arg Pro Asp
            580                 585                 590
Phe Phe Lys Asp Asp Gln Leu Phe Ile Val Leu Glu Phe Glu Phe Gly
            595                 600                 605
Gly Ile Asp Leu Glu Gln Met Arg Thr Lys Leu Ser Ser Leu Ala Thr
            610                 615                 620
Ala Lys Ser Ile Leu His Gln Leu Thr Ala Ser Leu Ala Val Ala Glu
625                 630                 635                 640
Ala Ser Leu Arg Phe Glu His Arg Asp Leu His Trp Gly Asn Val Leu
                645                 650                 655
Leu Lys Lys Thr Ser Leu Lys Lys Leu His Tyr Thr Leu Asn Gly Lys
            660                 665                 670
Ser Ser Thr Ile Pro Ser Cys Gly Leu Gln Val Ser Ile Ile Asp Tyr
            675                 680                 685
Thr Leu Ser Arg Leu Glu Arg Asp Gly Ile Val Val Phe Cys Asp Val
            690                 695                 700
Ser Met Asp Glu Asp Leu Phe Thr Gly Asp Gly Asp Tyr Gln Phe Asp
705                 710                 715                 720
Ile Tyr Arg Leu Met Lys Lys Glu Asn Asn Arg Trp Gly Glu Tyr
                725                 730                 735
His Pro Tyr Ser Asn Val Leu Trp Leu His Tyr Leu Thr Asp Lys Met
            740                 745                 750
Leu Lys Gln Met Thr Phe Lys Thr Lys Cys Asn Thr Pro Ala Met Lys
            755                 760                 765
Gln Ile Lys Arg Lys Ile Gln Glu Phe His Arg Thr Met Leu Asn Phe
            770                 775                 780
Ser Ser Ala Thr Asp Leu Leu Cys Gln His Ser Leu Phe Lys
785                 790                 795
```

<210> SEQ ID NO 18
<211> LENGTH: 2820
<212> TYPE: DNA
<213> ORGANISM: Homo sapiens

<400> SEQUENCE: 18

```
gcgtttgaac ctcttggcgg gtgccggcca tggcggcttc gctcccggga cctgggagcc      60
ggcttttccg cacatatggg gctgcggacg gcaggagaca gcggcggccg ggccgggaag     120
ccgcgcagtg gttcccgccg caggaccgga ggcgtttctt caacagcagc ggcagcagcg     180
acgcagcat cggcgacccc tcgcagtccg acgatcctga cgatcccgac gaccccgact     240
tccccggcag cccggtgagg cggcggcgga ggtgtcccgg cggccgagtg cccaaggacc     300
ggcccagcct gaccgtgacc ccaaagcgct ggaagctgcg agctcgccca gcctaaccg      360
tgaccccaag acgcctgggg ctgcgagctc ggccccgca gaagtgcagc acaccctgcg     420
gcccgctccg acttccgccc ttccccagcc gcgactccgg ccgcctcagc ccggacctca     480
```

-continued

```
gcgtgtgcgg ccagcccagg gacggcgacg agctgggcat cagtgcctcc ctgttcagct      540
ctctggcctc gccctgcccc gggtccccaa cgccaaggga cagtgtcatc tcgatcggca      600
cctccgcctg tctggttgca gcctcagccg tcccgagcga cctccacctc ccagaagtct      660
ccctggaccg agcatctctc ccctgctccc aggaggaagc gacaggagga gccaaggaca      720
ccaggatggt ccaccaaacc cgcgccagcc tcaggtcagt tctctttggc cttatgaact      780
caggaacccc tgaggattct gagtttcggg cagatgggaa gaatatgaga gagtcctgct      840
gtaaaaggaa actggtggtg ggaaatggac cagagggtcc aggtctgtca agcacaggca      900
agaggagggc cacaggccag gactcttgtc aagagagagg gcttcaagag gccgtccgga      960
gagagcatca ggaggccagt gttcccaagg gccgcattgt gccaagggga acagacaggc     1020
tggagagaac tagatcaagc cggaagagca acatcagga ggcaacggaa acctctctcc      1080
tccattccca ccgctttaaa aagggccaaa agctgggaaa agattcgttc cccacccagg     1140
acctgactcc tttacagaat gcctgctttt ggaccaaaac cagggcttcc ttcagtttcc     1200
acaagaagaa aattgtgact gatgtgtcag aggtctgcag catctatacc actgccactt     1260
ctctctctgg atccctccta tcagaatgtt caaaccggcc tgtcatgaac agaacaagtg     1320
gtgctccgtc ctcttggcac tcctcctcta tgtatttgct aagccccta aacactctaa      1380 gtatttcaaa caaaaaggca tctgatgctg aaaaggttta tggggaatgc agtcagaagg     1440
gtcctgtccc ctttagccat tgccttccca cagaaaaact gcaacgctgt gagaagattg     1500
gggaaggggt gtttggcgaa gtgtttcaaa caattgctga tcacacaccc gtagccataa     1560
aaatcattgc tattgaagga ccagatttag tcaatggatc ccatcagaaa acctttgagg     1620
aaatcctgcc agagatcatc atctccaaag agttgagcct cttatccggt gaagtgtgca     1680
accgcacaga aggctttatc gggctgaact cagtgcactg tgtccaggga tcttaccctc     1740
ccttgctcct caaagcctgg gatcactata attcaaccaa aggctctgca atgaccggc      1800 ctgattttttt taaagacgac cagctcttca ttgtgctgga atttgagttt ggagggattg     1860
acttagagca aatgcgaacc aagttgtctt ccttggctac tgcaaagagc attctacacc     1920
agctcacagc ctccctcgca gtggcagagg catcactgcg ctttgagcac cgagacttac     1980
actgggggaa cgtgctctta aagaaaacca gcctcaaaaa actccactac ccctcaatg      2040 ggaagagcag cactatcccc agctgtgggt tgcaagtgag catcattgac tacaccctgt     2100
cgcgcttgga acgggatggg attgtggttt tctgtgacgt ttccatggat gaggacctgt     2160
ttaccggtga cggtgactac cagtttgaca tctacaggct catgaagaag gagaataaca     2220
accgctgggg tgaatatcac ccttatagta atgtgctctg gttacattac ctgcagacga     2280
agatgctgaa acaaatgacc ttcaagacta aatgtaacac tcctgccatg aagcaaatta     2340
agagaaaaat ccaggagttc cacaggacaa tgctgaactt cagctctgcc actgacttgc     2400
tctgccagca cagtctgttt aagtaagcta aatgtatctt actgccccga atgagagga      2460 gactggtctt gaagcctctg gtgctgtttc aacctccgtc cccacaggag ggtggaactc     2520
ccattctcac aggtttccag tcagcttttc aaacaagaat tttgtttcca aatggaaact     2580
gaaatatttg ttgaaatgtt taaatttgct gataacaaat gttctgaaag aagtaaacta     2640
gccgggcgca gtggcgtgcg cctgtagtcc cagctactcg ggaggctgag gcaggaggat     2700
cgcttgagcc caagagttca tatctagcct ggtcaacata gcaagacccc tgtctctatt     2760
tttttaaata aataaactac atgtgaaaac aaaaaaaaaa aaaaaaaaaa aaaaaaaaaa     2820
```

<210> SEQ ID NO 19
<211> LENGTH: 136
<212> TYPE: PRT
<213> ORGANISM: Homo sapiens

<400> SEQUENCE: 19

Met Ala Arg Thr Lys Gln Thr Ala Arg Lys Ser Thr Gly Gly Lys Ala
1               5                   10                  15
Pro Arg Lys Gln Leu Ala Thr Lys Ala Ala Arg Lys Ser Ala Pro Ala
            20                  25                  30
Thr Gly Gly Val Lys Lys Pro His Arg Tyr Arg Pro Gly Thr Val Ala
        35                  40                  45
Leu Arg Glu Ile Arg Arg Tyr Gln Lys Ser Thr Glu Leu Leu Ile Arg
    50                  55                  60
Lys Leu Pro Phe Gln Arg Leu Val Arg Glu Ile Ala Gln Asp Phe Lys
65                  70                  75                  80
Thr Asp Leu Arg Phe Gln Ser Ser Ala Val Met Ala Leu Gln Glu Ala
                85                  90                  95
Cys Glu Ala Tyr Leu Val Gly Leu Phe Glu Asp Thr Asn Leu Cys Ala
            100                 105                 110
Ile His Ala Lys Arg Val Thr Ile Met Pro Lys Asp Ile Gln Leu Ala
        115                 120                 125
Arg Arg Ile Arg Gly Glu Arg Ala
    130                 135

<210> SEQ ID NO 20
<211> LENGTH: 472
<212> TYPE: DNA
<213> ORGANISM: Homo sapiens

<400> SEQUENCE: 20
atggctcgta ctaaacagac agctcggaaa tccaccggcg gtaaagcgcc acgcaagcag      60
ctggctacca aggctgctcg caagagcgcg ccggctaccg gcggcgtgaa aaagcctcac     120
cgttaccgcc cgggcactgt ggctctgcgc gagatccgcc gctaccaaaa gtcgaccgag     180
ttgctgattc ggaagctgcc gttccagcgc ctggtgcgag aaatcgccca agacttcaag     240
accgatcttc gcttccagag ctctgcggtg atggcgctgc aggaggcttg tgaggcctac     300
ttggtagggc tctttgagga cacaaacctt tgcgccatcc atgctaagcg agtgactatt     360
atgcccaaag acatccagct cgctcgccgc attcgcggag aaagagcgta aatgtaaagt     420
cactttttca tcagtcttaa aacccaaagg ctcttttcag agccacccac tt             472

<210> SEQ ID NO 21
<211> LENGTH: 130
<212> TYPE: PRT
<213> ORGANISM: Homo sapiens

<400> SEQUENCE: 21

Thr Ala Arg Lys Ser Thr Gly Gly Lys Ala Pro Arg Lys Gln Leu Ala
1               5                   10                  15
Thr Lys Ala Ala Arg Lys Ser Ala Pro Ala Thr Gly Gly Val Lys Lys
            20                  25                  30
Pro His Arg Tyr Arg Pro Gly Thr Val Ala Leu Arg Glu Ile Arg Arg
        35                  40                  45
Tyr Gln Lys Ser Thr Glu Leu Leu Ile Arg Lys Leu Pro Phe Gln Arg
    50                  55                  60

-continued

```
Leu Val Arg Glu Ile Ala Gln Asp Phe Lys Thr Asp Leu Arg Phe Gln
65                  70                  75                  80

Ser Ser Ala Val Met Ala Leu Gln Glu Ala Cys Glu Ala Tyr Leu Val
                85                  90                  95

Gly Leu Phe Glu Asp Thr Asn Leu Cys Ala Ile His Ala Lys Arg Val
            100                 105                 110

Thr Ile Met Pro Lys Asp Ile Gln Leu Ala Arg Arg Ile Arg Gly Glu
        115                 120                 125

Arg Ala
    130
```